(12) United States Patent
Takashino et al.

(10) Patent No.: US 8,348,947 B2
(45) Date of Patent: Jan. 8, 2013

(54) TREATMENT SYSTEM, AND TREATMENT METHOD FOR LIVING TISSUE USING ENERGY

(75) Inventors: Tomoyuki Takashino, Hino (JP); Koji Iida, Sagamihara (JP); Toru Nagase, Tachikawa (JP)

(73) Assignee: Olympus Medical Systems Corp. (JP)

( * ) Notice: Subject to any disclaimer, the term of this patent is extended or adjusted under 35 U.S.C. 154(b) by 1272 days.

(21) Appl. No.: 12/109,951

(22) Filed: Apr. 25, 2008

(65) Prior Publication Data

US 2009/0270852 A1 Oct. 29, 2009

(51) Int. Cl.
*A61B 18/18* (2006.01)
*A61B 18/08* (2006.01)

(52) U.S. Cl. ............... 606/51; 606/33; 606/27

(58) Field of Classification Search ........... 606/45–52
See application file for complete search history.

(56) References Cited

U.S. PATENT DOCUMENTS

| | | | |
|---|---|---|---|
| 5,443,463 | A | 8/1995 | Stern et al. |
| 5,647,871 | A | 7/1997 | Levine et al. |
| 5,951,546 | A | 9/1999 | Lorentzen |
| 6,500,176 | B1 | 12/2002 | Truckai et al. |
| 6,953,461 | B2 | 10/2005 | McClurken et al. |
| 2005/0072827 | A1 | 4/2005 | Mollenauer |
| 2005/0113828 | A1 | 5/2005 | Shields et al. |
| 2007/0102472 | A1 | 5/2007 | Shelton, IV |
| 2008/0195090 | A1 | 8/2008 | Takashino et al. |
| 2008/0195091 | A1 | 8/2008 | Takashino et al. |

FOREIGN PATENT DOCUMENTS

| | | |
|---|---|---|
| EP | 1 532 933 A1 | 5/2005 |
| EP | 2 106 762 A1 | 10/2009 |
| JP | 11-070123 | 3/1999 |
| JP | 2003-235865 | 8/2003 |
| JP | 2007-075468 | 3/2007 |
| WO | WO 99/12488 | 3/1999 |
| WO | WO 02/058544 | 8/2002 |
| WO | WO 02/080784 | 10/2002 |
| WO | WO 2004/082495 | 9/2004 |
| WO | WO 2008/120822 A1 | 10/2008 |
| WO | WO 2009/022614 A1 | 2/2009 |
| WO | WO 2009/130752 A1 | 10/2009 |

OTHER PUBLICATIONS

Search Report issued by European Patent Office in connection with corresponding application No. EP 09 00 5637 on Dec. 16, 2009.
Japanese Office Action mailed Sep. 4, 2012 in connection with corresponding.
Japanese Patent Application No. 2009-051144 and English translation thereof.

*Primary Examiner* — Linda Dvorak
*Assistant Examiner* — Amanda Scott
(74) *Attorney, Agent, or Firm* — Ostrolenk Faber LLP

(57) ABSTRACT

A treatment system that applies energy to a living tissue to treat the same, the treatment system includes
 a sealing member which joins desired sealed regions of at least two living tissues when the energy is applied to the living tissues in a state where the desired regions are sealed,
 a maintaining member which maintains living tissues near the sealed regions in a contact state when the energy is applied to the living tissues in a state where the tissues near the regions sealed by the sealing member are in contact with each other,
 at least one first control section which controls an output of the energy that is applied to the sealing member, and
 at least one second control section which controls an output of the energy that is applied to the maintaining member.

11 Claims, 15 Drawing Sheets

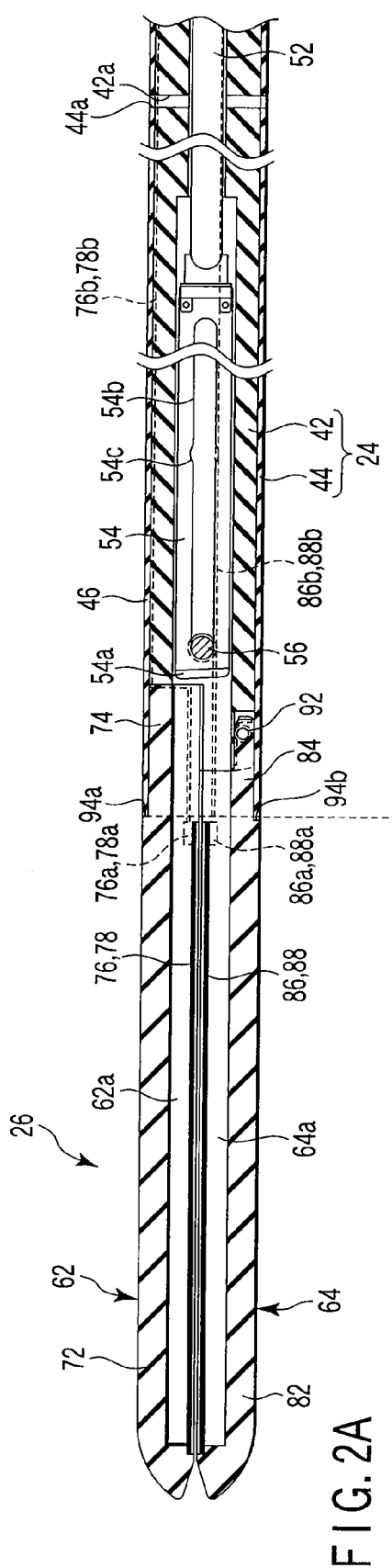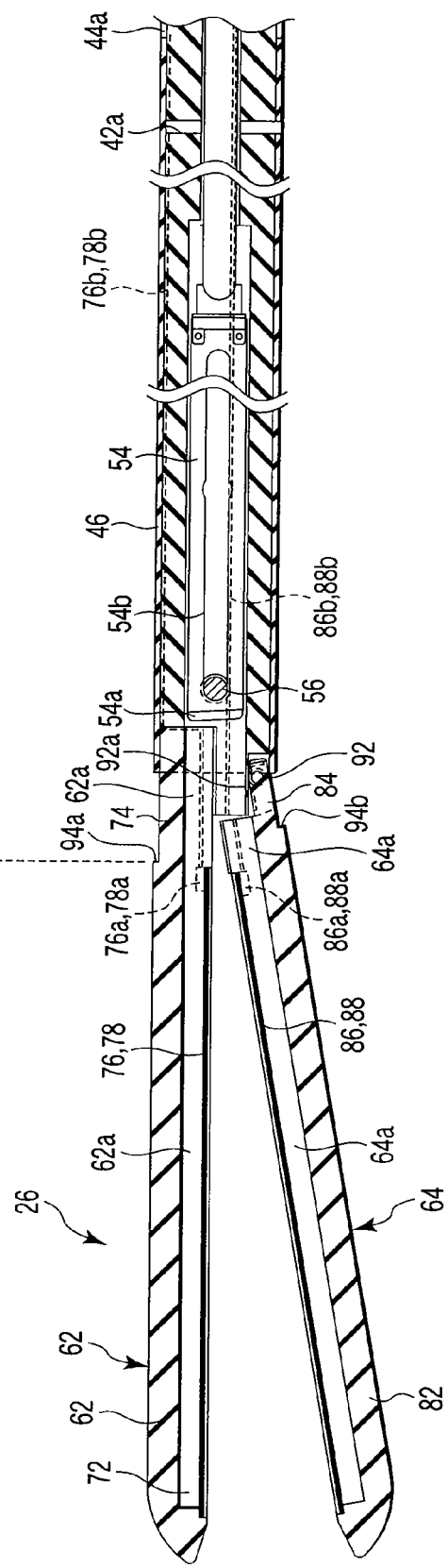

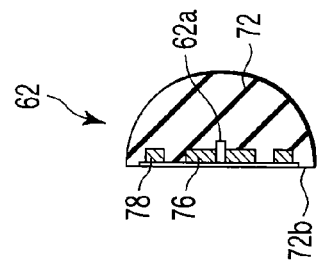
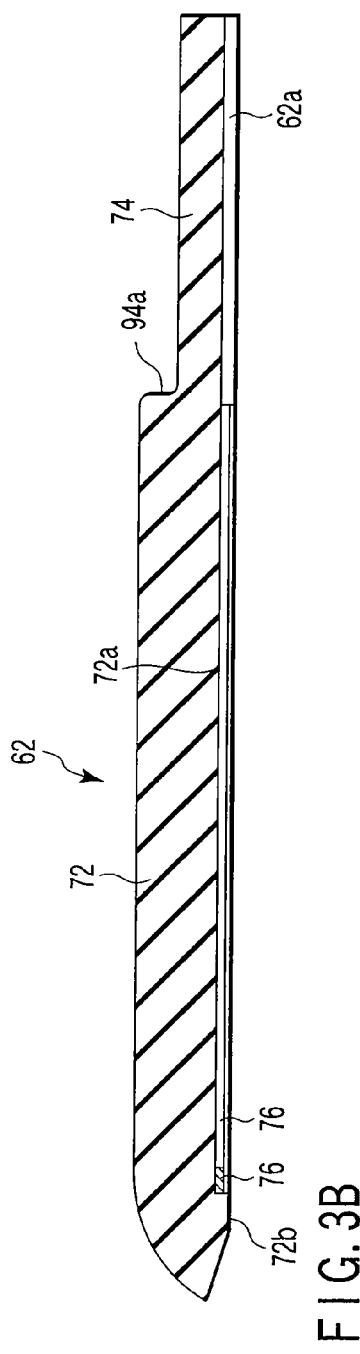
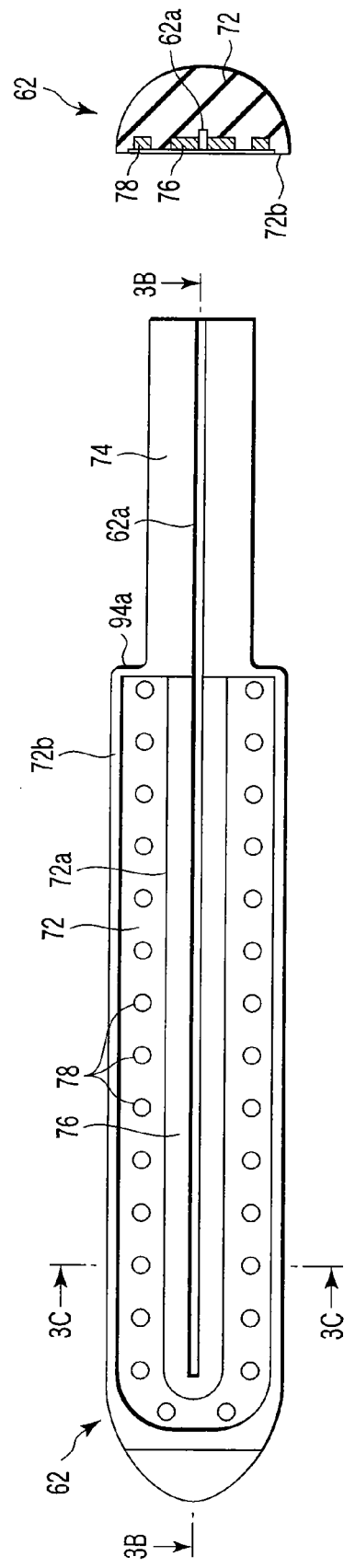

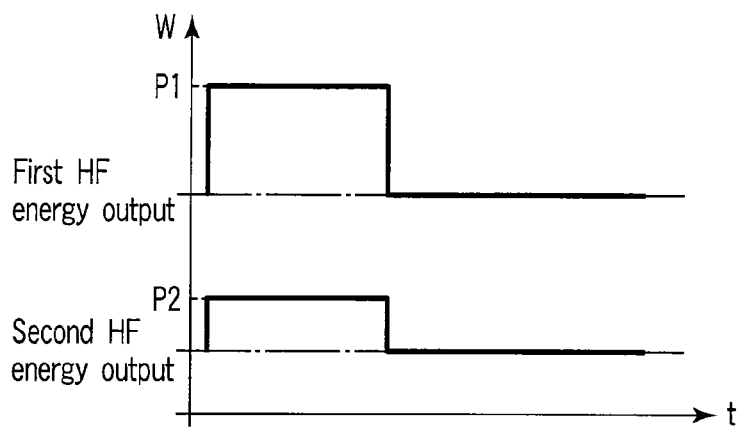
F I G. 6A
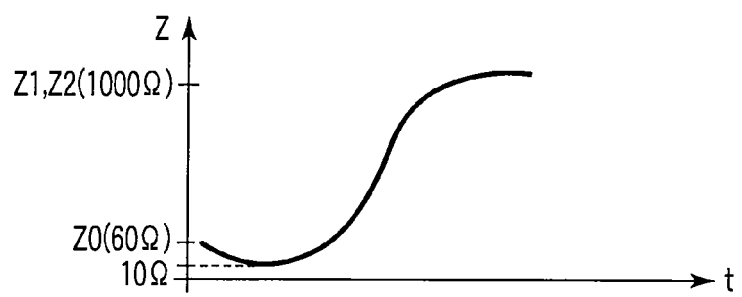
F I G. 6B
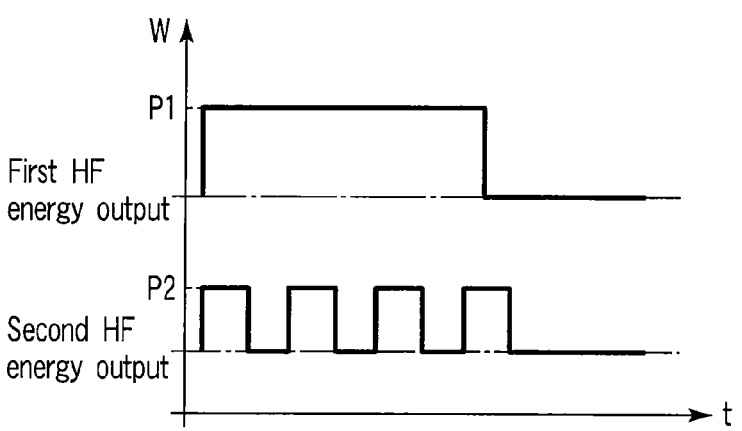
F I G. 6C
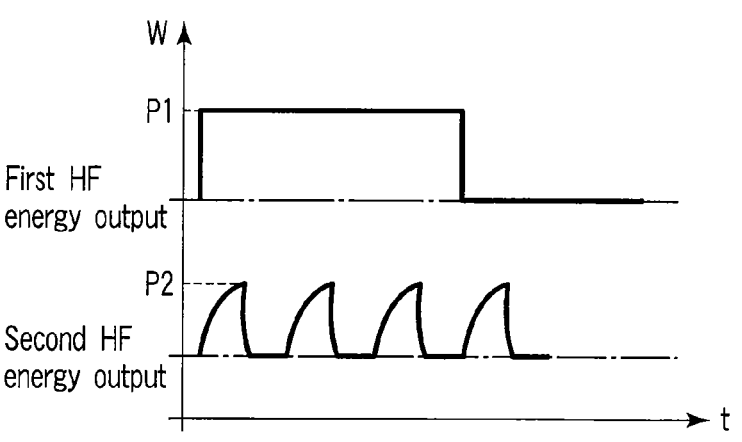
F I G. 6D

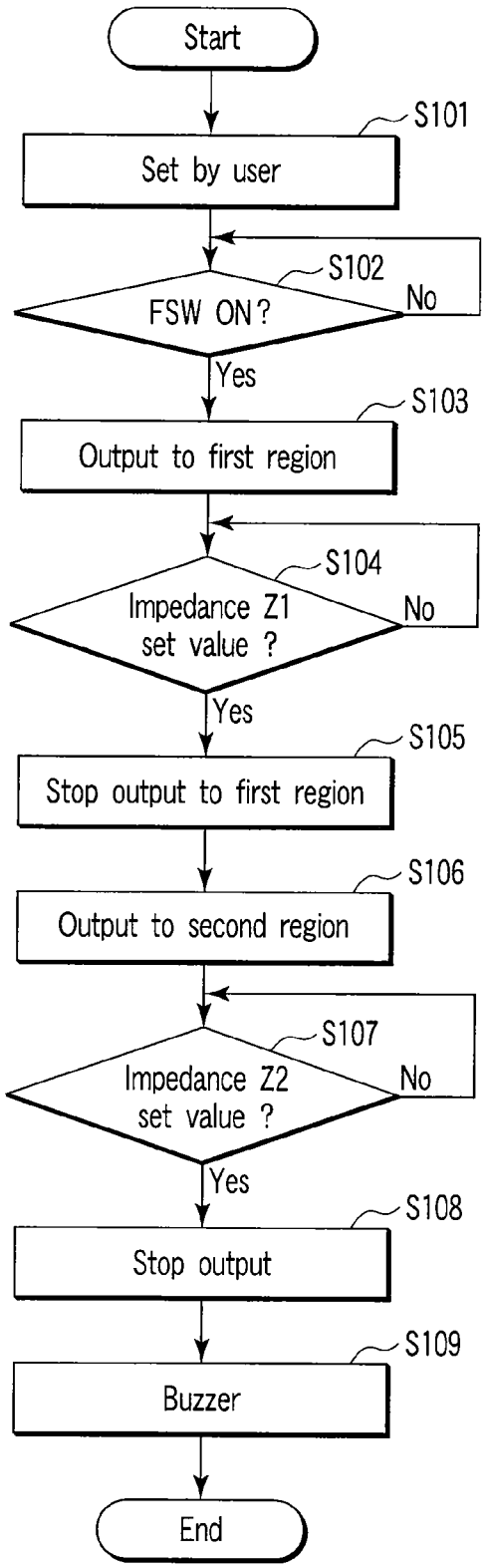
F I G. 8

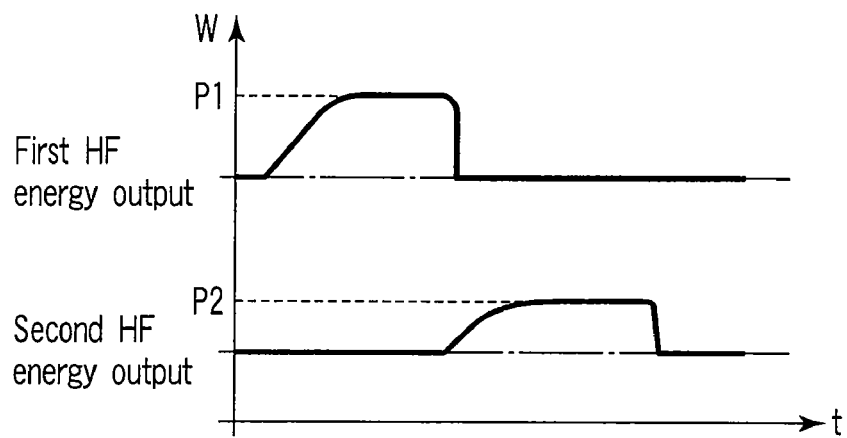
F I G. 9A
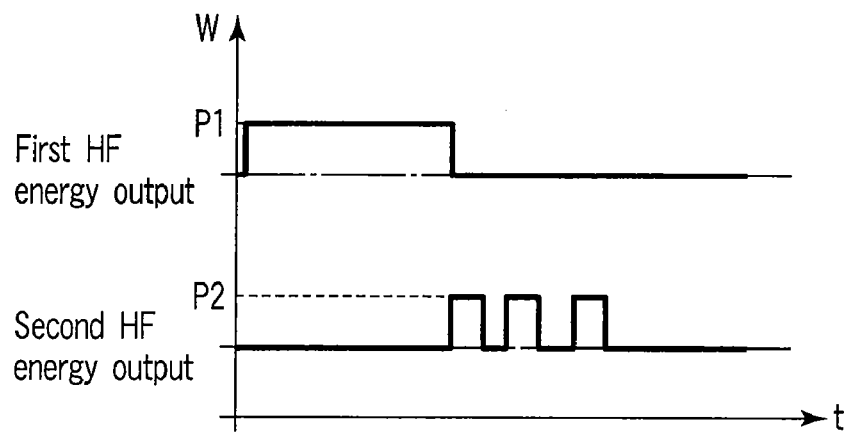
F I G. 9B
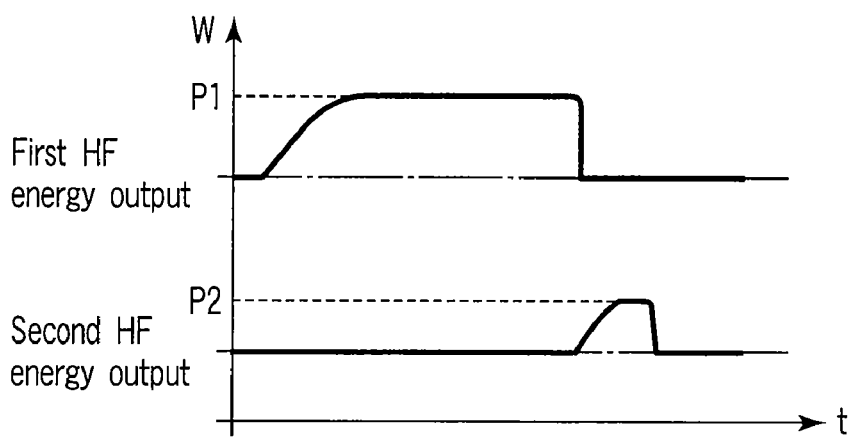
F I G. 9C

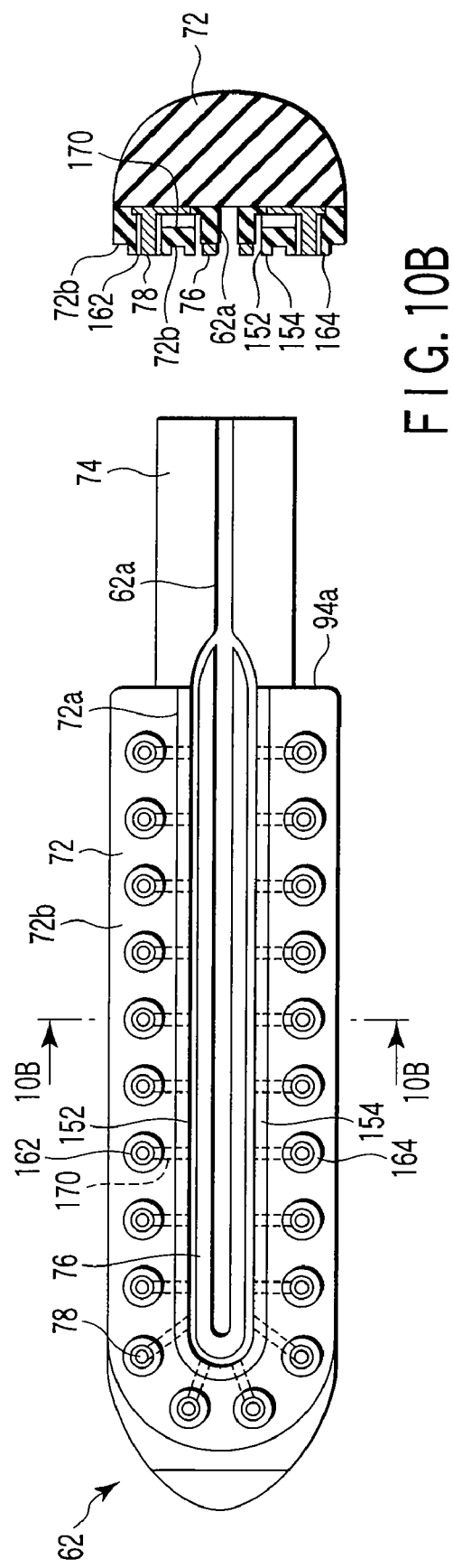
FIG. 10A
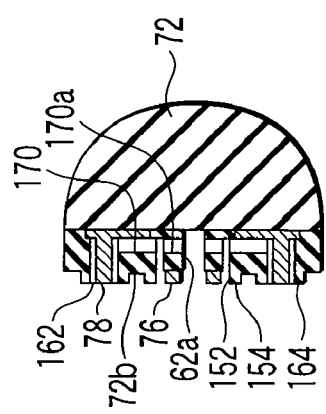
FIG. 10B
FIG. 10C

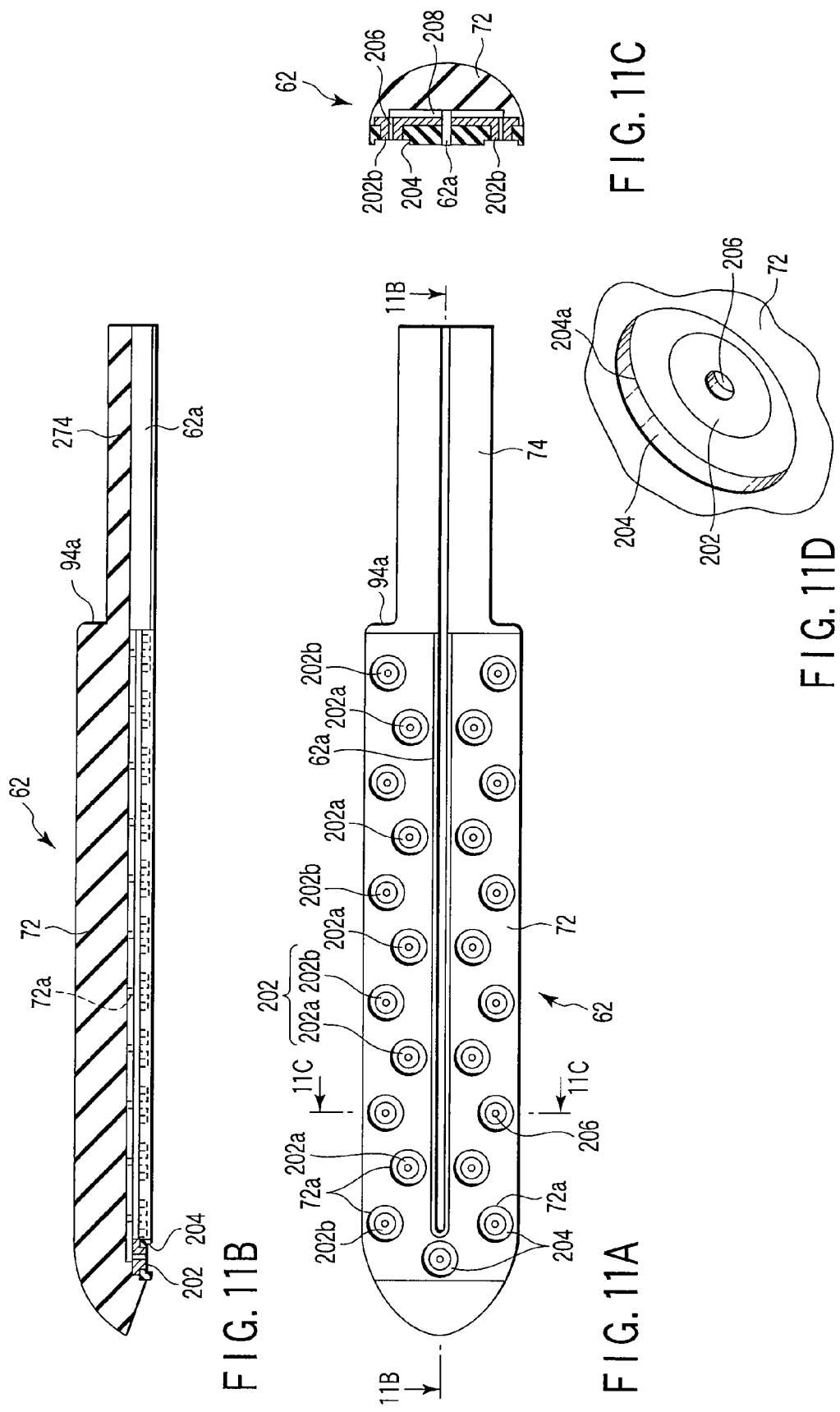

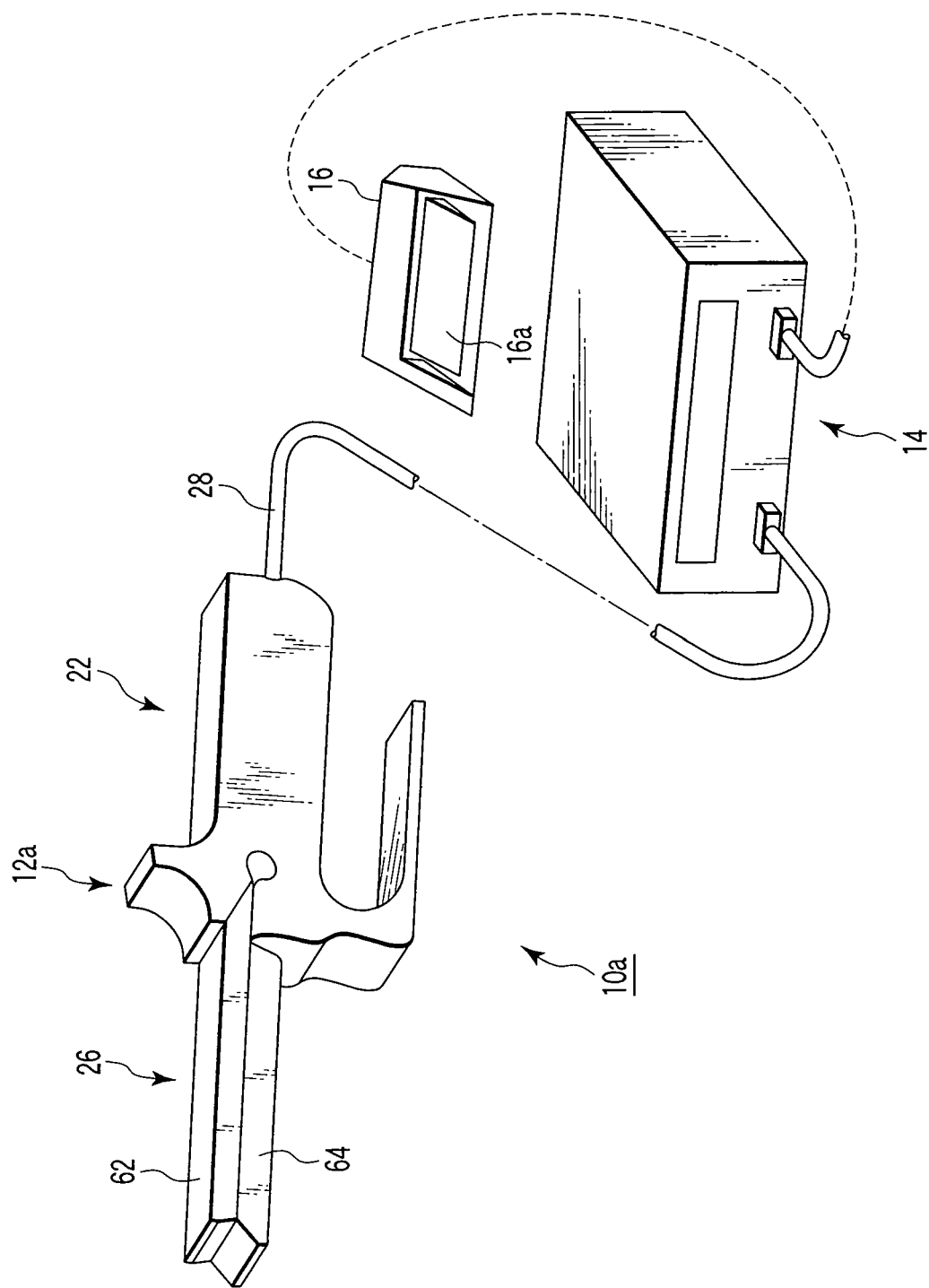
F I G. 12

TREATMENT SYSTEM, AND TREATMENT METHOD FOR LIVING TISSUE USING ENERGY

BACKGROUND OF THE INVENTION

1. Field of the Invention

The present invention relates to a treatment system that uses energy to treat a living tissue, and a treatment method for a living tissue by use of energy.

2. Description of the Related Art

U.S. Pat. No. 5,443,463 discloses a coagulation forceps having a plurality of electrodes arranged therein. In this forceps, RF Power Out from one electrosurgical power supply is transmitted to the respective electrodes through an indifferent electrode connector. Therefore, the coagulation forceps uses radio-frequency energy to treat a living tissue through the electrodes controlled in the same state.

BRIEF SUMMARY OF THE INVENTION

According to a first aspect of the present invention, there is provided a treatment system that applies energy to a living tissue to treat the living tissue, comprising:

a sealing member which joins desired sealed regions of at least two living tissues when the energy is applied to the living tissues in a state where the desired regions are sealed;

a maintaining member which maintains living tissues near the sealed regions in a contact state when the energy is applied to the living tissues in a state where the tissues near the regions sealed by the sealing member are in contact with each other;

at least one first control section which controls an output of the energy that is applied to the sealing member; and at least one second control section which controls an output of the energy that is applied to the maintaining member.

According to a second aspect of the present invention, there is provided a treatment method of giving a living tissue a treatment, comprising:

sealing desired regions of at least two living tissues;

maintaining the at least two living tissues in a contact state near a position at which the desired regions of the at least two living tissues are sealed; and supplying a controlled energy to maintain a state where the desired regions of the at least two living tissues are sealed and a state where the at least two living tissues are maintained to be in contact with each other.

According to a third aspect of the present invention, there is provided a treatment instrument which applies energy to a living tissue to treat the same, comprising:

a sealing member which joins desired sealed regions of at least two living tissues when the energy is applied to the desired sealed regions in a state where the desired regions of the at least two living tissues are sealed; and a maintaining member which is provided independently from the sealing member and maintains living tissues near the sealed region in a contact state when energy is applied separately from the sealing member in a state where the tissues near the region sealed by the sealing member are in contact with each other.

Additional objects and advantages of the invention will be set forth in the description which follows, and in part will be obvious from the description, or may be learned by practice of the invention. The objects and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic vertical sectional view showing a shaft of an energy treatment instrument, and a first holding member and a second holding member in a state where a holding portion is closed in the treatment system according to the first embodiment;

FIG. 2B is a schematic vertical sectional view showing the shaft of the energy treatment instrument, and the first holding member and the second holding member in a state where the holding portion is opened in the treatment system according to the first embodiment;

FIG. 3A is a schematic plan view showing the first holding member on a side close to the second holding member in the holding portion of the energy treatment instrument in the treatment system according to the first embodiment;

FIG. 3B is a schematic vertical sectional view showing the first holding member in the holding portion of the energy treatment instrument in the treatment system according to the first embodiment taken along a line 3B-3B in FIG. 3A;

FIG. 3C is a schematic lateral cross-sectional view showing the first holding member in the holding portion of the energy treatment instrument in the treatment system according to the first embodiment taken along a line 3C-3C in FIG. 3A;

FIG. 6A is a schematic graph showing an example of a way of inputting radio-frequency energy to a living tissue with respect to a time when a treatment system according to a modification of the first embodiment is used to give a treatment using the radio-frequency energy to the living tissue;

FIG. 6B is a schematic graph showing a change in an impedance with respect to a time at which predetermined radio-frequency energy is input to a living tissue when the treatment system according to the first embodiment is used to give a treatment using the radio-frequency energy to the living tissue;

FIG. 6C is a schematic graph showing an example of a way of inputting radio-frequency energy to a living tissue with respect to a time when a treatment system according to a modification of the first embodiment is used to give a treatment using the radio-frequency energy to the living tissue;

FIG. 6D is a schematic graph showing an example of a way of inputting radio-frequency energy to a living tissue with respect to a time when a treatment system according to a modification of the first embodiment is used to give a treatment using the radio-frequency energy to the living tissue;

FIG. 8 is a schematic flowchart when a treatment system according to a first modification of the first embodiment is used to give a treatment using radio-frequency energy to a living tissue;

FIG. 9A is a schematic graph showing an example of a way of inputting radio-frequency energy to a living tissue with respect to a time when the treatment system according to the first modification of the first embodiment is used to give a treatment using the radio-frequency energy to the living tissue;

FIG. 9B is a schematic graph showing an example of a way of inputting radio-frequency energy to a living tissue with respect to a time when the treatment system according to the first modification of the first embodiment is used to give a treatment using the radio-frequency energy to the living tissue;

FIG. 9C is a schematic graph showing an example of a way of inputting radio-frequency energy to a living tissue with respect to a time when the treatment system according to the first modification of the first embodiment is used to give a treatment using the radio-frequency energy to the living tissue;

FIG. 10A is a schematic plan view showing a first holding member on a side close to a second holding member in a holding portion of an energy treatment instrument in a treatment system according to a second modification of the first embodiment;

FIG. 10B is a schematic lateral cross-sectional view showing the first holding member in the holding portion of the energy treatment instrument in the treatment system according to the second modification of the first embodiment taken along a line 10B-10B depicted in FIG. 10A;

FIG. 10C is a schematic lateral cross-sectional view showing a modification of the first holding member in the holding portion of the energy treatment instrument in the treatment system according to the second modification of the first embodiment taken along a line 10B-10B depicted in FIG. 10A;

FIG. 11A is a schematic plan view showing a first holding member on a side close to a second holding member in a holding portion of an energy treatment instrument in a treatment system according to a third modification of the first embodiment;

FIG. 11B is a schematic vertical sectional view showing the first holding member in the holding portion of the energy treatment instrument in the treatment system according to the third modification of the first embodiment taken along a line 11B-11B depicted in FIG. 11A;

FIG. 11C is a schematic lateral cross-sectional view showing the first holding member in the holding portion of the energy treatment instrument in the treatment system according to the third modification of the first embodiment taken along a line 11C-11C depicted in FIG. 11A;

FIG. 11D is a schematic view showing a part near an electrode arranged in the first holding member in the holding portion of the energy treatment instrument in the treatment system according to the third modification of the first embodiment;

FIG. 12 is a schematic view showing a modification of the treatment system according to the first embodiment;

DETAILED DESCRIPTION OF THE INVENTION

The best mode for carrying out the present invention will now be explained hereinafter with reference to the drawings.

[First Embodiment]

A first embodiment will now be explained with reference to FIGS. 1A to 7D.

Here, an energy treatment instrument (a treatment instrument) will be explained while taking a linear type surgical instrument 12 that gives a treatment through, e.g., an abdominal wall as an example.

Figures 1A, 1B:
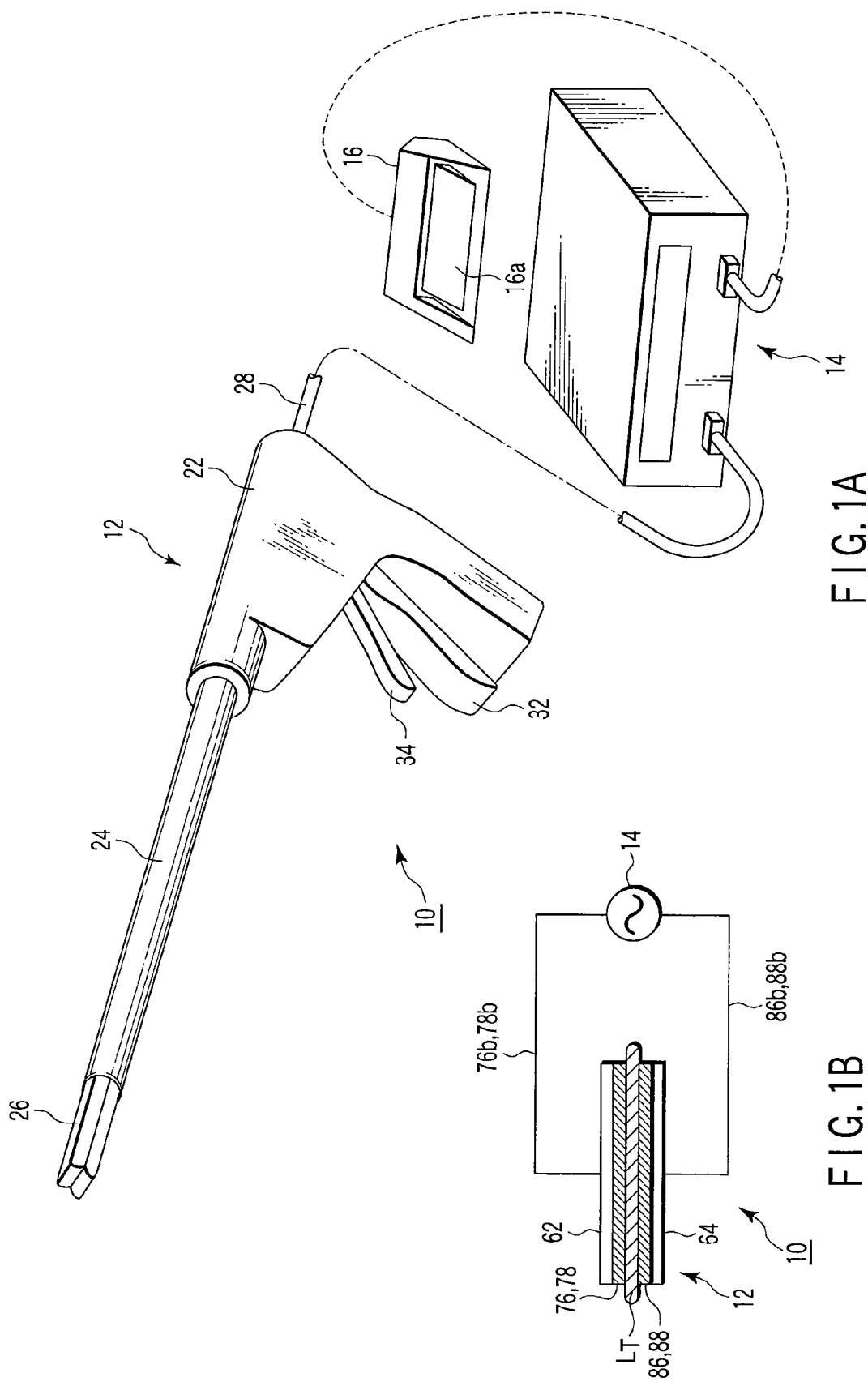
FIG. 1A is a schematic view showing a treatment system according to a first embodiment of the present invention.
FIG. 1B is a schematic view when giving a surgical instrument in the treatment system according to the first embodiment supplies a bipolar type radio-frequency energy to treat a living tissue.

As shown in FIG. 1A, a treatment system 10 includes an energy treatment instrument 12, an energy source (a control section 14), and a footswitch 16.

The energy treatment instrument 12 includes a handle 22, a shaft 24, an openable/closable holding portion 26. The handle 22 is connected with the energy source 14 through a cable 28. The footswitch (which may be a hand switch) 16 is connected with the energy source 14.

It is to be noted that the footswitch 16 includes a pedal 16a. Therefore, when an operator operates the pedal 16a of the footswitch 16, the turning on/off of the supply of energy to the surgical instrument 12 from the energy source 14 is switched. When the pedal 16a is pressed, an output is produced based on a state where radio-frequency energy is appropriately set (a state where an energy output amount, an energy output timing, and others are controlled). When the pedal 16a is released, an output of the radio-frequency energy is forcibly stopped.

The handle 22 is formed into a shape that can be easily grasped by an operator, and it is formed into, e.g., substantially an L-shape. The shaft 24 is arranged on one end of the handle 22. The above-explained cable 28 is extended from a proximal end of the handle 22 coaxially with the shaft 24.

On the other hand, the other end side of the handle 22 is a grasping portion that is grasped by an operator. The handle 22 includes a holding portion opening/closing knob 32 to be aligned on the other end side. The holding portion opening/closing knob 32 is coupled with a proximal end of a later-explained sheath 44 (see FIGS. 2A and 2B) of the shaft 24 at a substantially central part of the handle 22. When the holding portion opening/closing knob 32 is moved closer to or away from the other end of the handle 22, the sheath 44 moves along an axial direction thereof. The handle 22 further includes a cutter driving knob 34 that moves a later-explained cutter 54 in a state where it is arranged in parallel with the holding portion opening/closing knob 32.

As shown in FIGS. 2A and 2B, the shaft 24 includes a cylindrical body 42 and the sheath 44 arranged to be slidable on an outer side of the cylindrical body 42. The cylindrical body 42 is fixed to the handle 22 at a proximal end portion (see FIG. 1). The sheath 44 can slide along an axial direction of the cylindrical body 42.

A concave portion 46 is formed on the outer side of the cylindrical body 42 along the axial direction. A first electrode energization line 76b connected with a later-explained first continuous electrode (an output section) 76 and a second electrode energization line 78b connected with later-explained first discrete electrodes (the output section) 78 are arranged in the concave portion 46. Although not shown, it is preferable that the first and second electrode energization lines 76b and 78b are arranged between later-explained first and second electrode connectors 76a and 78a and the cable 28 and they are bundled as one from the first and second connectors 76a and 78a toward the cable 28 through the first electrode energization line 75b and the second electrode energization line 78b.

A third electrode energization line 86b connected with a later-explained second continuous electrode (the output section) 86 and a fourth electrode energization line 88b connected with later-explained second discrete electrodes (the output section) 88 are inserted in the cylindrical body 42. Although not shown, it is preferable that the third and fourth electrode energization lines 86b and 88b are arranged between later-explained third and fourth electrode connectors 86a and 88a and the cable 28 and they are bundled as one from the third and fourth electrode connectors 86a and 88a toward the cable 28.

A driving rod 52 is arranged in the cylindrical body 42 of the shaft 24 to be movable along the axial direction. A thin-plate-like cutter (a treatment auxiliary instrument) 54 is arranged at a distal end of the driving rod 52. Therefore, when the cutter driving knob 34 is operated, the cutter 54 moves through the driving rod 52.

A blade 54a is formed at a distal end of the cutter 54, and a distal end of the driving rod 52 is fixed to a proximal end of the cutter 54. A long groove 54b is formed between the distal end and the proximal end of the cutter 54. A movement restriction pin 56 extending in a direction perpendicular to the axial direction of the shaft 24 is fixed to the cylindrical body 42 of the shaft 24. Therefore, the long grove 54b of the cutter 54 moves along the movement restriction pin 56. Then, the cutter 54 moves straightforward. At this time, the cutter 54 is arranged in a cutter guide groove (a flow path, a fluid discharge groove) 62a of a later-explained first holding member 62 and a cutter guide groove (a flow path, a fluid discharge groove) 64a of a second holding member 64.

It is to be noted that latching portions 54c that latch the movement restriction pin 56 and control movement of the cutter 54 are formed at least at three positions, i.e., one end, the other end, and a position between the one end and the other end of the long groove 54b of the cutter 54.

As shown in FIGS. 1A, 2A, and 2B, the holding portion 26 is arranged at the distal end of the shaft 24. As depicted in FIGS. 2A and 2B, the holding portion 26 includes a first holding member (a first jaw) 62 and a second holding member (a second jaw) 64.

It is preferable for each of the first holding member 62 and the second holding member 64 themselves to entirely have insulating properties. The first holding member 62 integrally includes a first holding member main body (which will be mainly referred to as a main body hereinafter) 72 and a base portion 74 provided at a proximal end portion of the main body 72. The cutter guide groove 62a that guides the cutter 54 is formed in the first holding member main body 72 and the base portion 74.

As shown in FIGS. 2A to 3D, a plurality of concave portions 72a and a holding surface 72b are formed in the main body 72 of the first holding member 62.

Further, one first continuous electrode 76 and a plurality of first discrete electrodes 78a are arranged in the plurality of concave portions 72a of the main body 72. That is, in the first holding member 62, the first continuous electrode 76 and the first discrete electrodes 78 are arranged as output members or energy discharge portions.

The first continuous electrode (a sealing member, a first joining member) 76 is continuously formed without discontinuity. The first continuous electrode 76 is continuously formed into, e.g., substantially a U-shape to have two end portions at the proximal end portion of the main body 72 of the first holding member 62. At least one of the two end portions of the first continuous electrode 76 is electrically connected with the first electrode connector 76a arranged at the one end portion. The first electrode connector 76a is connected with the cable 28 extended from the handle 22 through the first electrode energization line 76b. Furthermore, the first continuous electrode 76 is connected with a later-explained radio-frequency energy output circuit 104 of the energy source 14.

A cutter guide groove (which will be denoted by the same reference number 62a as the cutter guide groove 62a of the first holding member 62 for the convenience's sake) that guides the cutter 54 with the main body 72 and the base portion 74 of the first holding member 62 is formed between the two end portions of the first continuous electrode 76.

The first discrete electrodes (maintaining members, second joining members) 78 are discretely arranged on an outer side of the first continuous electrode 76. The plurality of first discrete electrodes 78 having the same shape are arranged along a substantially U-shaped virtual trajectory at practically equal intervals. The first discrete electrodes 78 are formed into, e.g., a circular. The first discrete electrodes 78 are arranged at substantially predetermined intervals, and each discrete electrode 78 is arranged at a position apart from the first continuous electrode 76 by an appropriate distance. Each first discrete electrode 78 is placed at a position that allows a living tissue $L_T$ between each first discrete electrode 78 and each second discrete electrode 88 of the second holding member 64 to be denatured due to heat when a treatment is given, but prevents the living tissue $L_T$ between the first discrete electrodes 78 of the first holding member 62 from being denatured due to heat as much as possible, and also avoids denaturalization of the living tissue between the first discrete electrodes 78 and the first continuous electrode 76 due to heat as much as possible.

Although not shown, the plurality of first discrete electrodes 78 are electrically connected with each other in the main body 72, and also electrically connected with the second electrode connector 78a provided in parallel with the first electrode connector 76a. The second electrode connector 78a is connected with the cable 28 extended from the handle 22 through the second electrode energization line 78b. Moreover, the first discrete electrodes 78 are connected with a later-explained second radio-frequency energy output circuit 106 of the energy source 14.

It is to be noted that the holding surface 72b of surfaces of the first continuous electrode 76 and the first discrete electrodes 78 is formed to be raised. The holding surface 72b is closer to a main body 82 of the opposed second holding member 64 than the surfaces of the first continuous electrode 76 and the first discrete electrodes 78 and comes into contact with a holding surface (which will be denoted by reference character 82b for the convenience's sake) of the main body 82 of the opposed second holding member 64.

The second holding member 64 integrally includes the second holding portion main body 82 and a base portion 84 provided at a proximal end portion of the main body 82. A cutter guide groove 64a that guides the cutter 54 is formed in the second holding member main body 82 and the base portion 84.

A concave portion (which will be designated by reference character 82a for the convenience's sake) and the holding surface 82b are formed in the main body 82 of the second holding member 64.

Additionally, a second continuous electrode 86 and the second discrete electrodes 88 are arranged in the concave portion 82a of the main body 82. That is, in the second holding member 64, the second continuous electrode 86 and the second discrete electrodes 88 are arranged as output members or energy discharge portions.

The second continuous electrode (a sealing member, a first joining member) 86 is arranged to be symmetrical to the first continuous electrode 76 arranged in the first holding member 62. Therefore, a cutter guide groove (which will be denoted by the same reference character 64a as the cutter guide groove 64a of the second holding member 64 for the convenience's sake) that guides the cutter 54 with the main body 82 and the base portion 84 of the second holding member 64 is formed between two end portions of the second continuous electrode 86. The second discrete electrodes 88 are arranged to be symmetrical to the first discrete electrodes 78 arranged in the first holding member 62. Therefore, a detailed description on the second continuous electrode 86 and the second discrete electrodes 88 will be omitted.

It is to be noted that the second continuous electrode 86 is electrically connected with the third electrode connector 86a arranged at the end portion facing the end portion opposite to the end portion at which the first electrode connector 76a is arranged. Further, the third electrode connector 86a is connected with the cable 28 extended from the handle 22 through the third electrode energization line 86b. Furthermore, the second continuous electrode 86 is connected with a later-explained first radio-frequency energy output circuit 104 of the energy source 14.

The second discrete electrodes 88 are electrically connected with the fourth electrode connector 88a arranged in parallel with the third electrode connector 86a. The fourth electrode connector 88a is connected with the cable 28 extended from the handle 22 through the fourth electrode energization line 88b. Moreover, the second discrete electrodes 88 are connected with a later-explained second radio-frequency energy output circuit 106 of the energy source 14.

It is to be noted that the cutter guide grooves 62a and 64a of the first and second holding members 62 and 64 are formed to face each other, and also formed along the axial direction of the shaft 24. Additionally, the two cutter guide grooves 62a and 64a can guide the single cutter 54.

Fluid discharge openings 42a and 44a from which a later-explained fluid, e.g., steam (a gas) or a liquid (a tissue fluid) is discharged are formed in the cylindrical body 42 and the sheath 44 of the shaft 24 of the energy treatment instrument 12 depicted in FIGS. 2A and 2B. These fluid discharge openings 42a and 44a are formed on the proximal end side of the shaft 24.

Although not shown here, it is also preferable for a connection mouth ring to be provided on an outer peripheral surface of the fluid discharge opening 44a of the sheath 44. At this time, the later-explained fluid is discharged through the cutter guide grooves 62a and 64a, the fluid discharge opening 42a of the cylindrical body 42 of the shaft 24, the fluid discharge opening 44a of the sheath 44 of the shaft 24, and the connection mouth ring. In this case, sucking the inside of the connection mouth ring enables readily discharging the fluid such as steam or a fluid emitted from the living tissue $L_T$ through the fluid discharge openings 42a and 44a.

It is to be noted that providing the fluid discharge openings 42a and 44a in the shaft 24 is preferable but providing them in the handle 22 rather than the shaft 24 is also preferable.

The base portion 74 of the first holding member 62 is fixed at the distal end portion of the cylindrical body 42 of the shaft 24. On the other hand, the base portion 84 of the second holding member 64 is supported to allow its swiveling motion at the distal end portion of the cylindrical body 42 of the shaft 24 by a support pin 92 arranged in a direction perpendicular to the axial direction of the shaft 24. The second holding member 64 can be opened/closed with respect to the first holding member 62 when swiveling around the axis of the support pin 92. The second holding member 64 is urged by an elastic member 92a, e.g., a leaf spring so that the second holding member 64 can be opened with respect to the first holding member 62.

Each of outer surfaces of the main bodies 72 and 82 of the first and second holding members 62 and 64 is formed into a smooth curved surface. Likewise, each of outer surfaces of the base portions 74 and 84 of the first and second holding members 62 and 64 is also formed into a smooth curved surface. In a state where the second holding member 64 is closed with respect to the first holding member 62, a cross section of each of the main bodies 72 and 82 of the respective holding members 62 and 64 is formed into substantially a circle or substantially an ellipse. In the state where the second holding member 64 is closed with respect to the first holding member 62, the holding surfaces 72b and 82b of the main bodies 72 and 82 of the first and second holding members 62 and 64 face each other, and each of the base portions 74 and 84 is formed into a cylinder. In this state, a diameter of the base end portion of each of the main bodies 72 and 82 of the first and second holding members 62 and 64 is larger than a diameter of each of the base portions 74 and 84. Further, steps 94a and 94b are formed between the main bodies 72 and 84 and the base portions 74 and 84, respectively.

Here, each of the first holding member 62 and the second holding member 64 has a substantially circular or substantially elliptic outer peripheral surface including each of the base portions 74 and 84 being substantially level with or slightly larger than an outer peripheral surface of the distal end portion of the cylindrical body 42 in diameter when the second holding member 64 is closed with respect to the first holding member 62. Therefore, the sheath 44 can slide with respect to the cylindrical body 42 to cover the base portions 74 and 84 of the first holding member 62 and the second holding member 64 with the distal end of the sheath 44. In this state, as shown in FIG. 2A, the first holding member 62 and the second holding member 64 are closed against an urging force of the elastic member 92a. On the other hand, when the sheath 44 slides toward the proximal end side of the cylindrical body 42 from the state where the base portions 74 and 84 of the first holding member 62 and the second holding member 64 are covered with the distal end of the sheath 44, the second holding member 64 is opened with respect to the first holding member 62 by the urging force of the elastic member 92a as shown in FIG. 2B.

Furthermore, in this embodiment, each of a clearance between the proximal end portions of the first continuous electrode 76 and a clearance between the proximal end portions of the second continuous electrode 86 is formed to have a size substantially equal to a width of each of the cutter guide grooves 62a and 64a of the first holding member 62 and the second holding member 64 (see FIG. 3D), but the clearance between the proximal end portions of the first continuous electrode 76 and the clearance between the proximal end portions of the second continuous electrode 86 can be appropriately set, respectively. That is, the first continuous electrode 76 and the second continuous electrode 86 may be provided at positions apart from edge portions of the cutter guide grooves 62a and 64a of the first holding member 62 and the second holding member 64, respectively.

Figure 4:
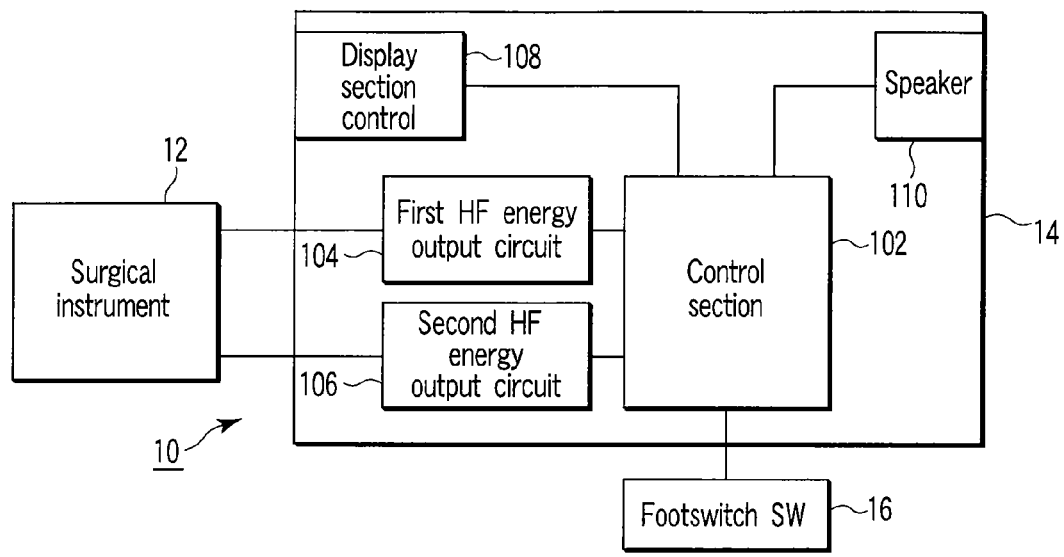
FIG. 4 is a schematic block diagram of the treatment system according to the first embodiment.

As shown in FIG. 4, a control section 102, the first radio-frequency energy output circuit (a first control section) 104, the second radio-frequency energy output circuit (a second control section) 106, a display section 108, and a speaker 110 are arranged in the energy source 14. The control section 102 is connected with the first radio-frequency energy output circuit 104, the second radio-frequency energy output circuit 106, the display section 108, and the speaker 110, and the control section 102 controls these members. The footswitch 16 is connected with the control section 102, and a treatment using the energy treatment instrument 12 is carried out when the footswitch 16 is turned on (when the pedal 16a is pressed), whilst the treatment is stopped when the footswitch 16 is turned off (when the pedal 16a is released from the pressed state). The display section 108 functions as setting means (a controller) when using the control section 102 to control an output amount (an output amount itself or a treatment to be given [e.g., a treatment for joining living tissues or a treatment for sealing openings of living tissues]) from each of the first radio-frequency energy output circuit 104 and the second radio-frequency energy output circuit 106 or an output timing for energy. Of course, the display section 108 has a function of displaying setting contents.

It is to be noted that the first radio-frequency energy output circuit 104 can output radio-frequency energy through the first and second continuous electrodes 76 and 86 and detect an impedance Z of a living tissue between the first and second continuous electrodes 76 and 86. The second radio-frequency energy output circuit 106 can output radio-frequency energy through the first and second discrete electrodes 78 and 88 and detect the impedance Z of the living tissue between the first and second discrete electrodes 78 and 88. That is, the first radio-frequency energy output circuit 104 and the first and second continuous electrodes 76 and 86 have a sensor function of measuring the impedance Z of the living tissue $L_T$ between the first and second continuous electrodes 76 and 86. The second radio-frequency energy output circuit 106 and the first and second discrete electrodes 78 and 88 have a sensor function of measuring the impedance Z of the living tissue $L_T$ between the first and second discrete electrodes 78 and 88.

A function of the treatment system 10 according to this embodiment will now be explained.

Figure 5:
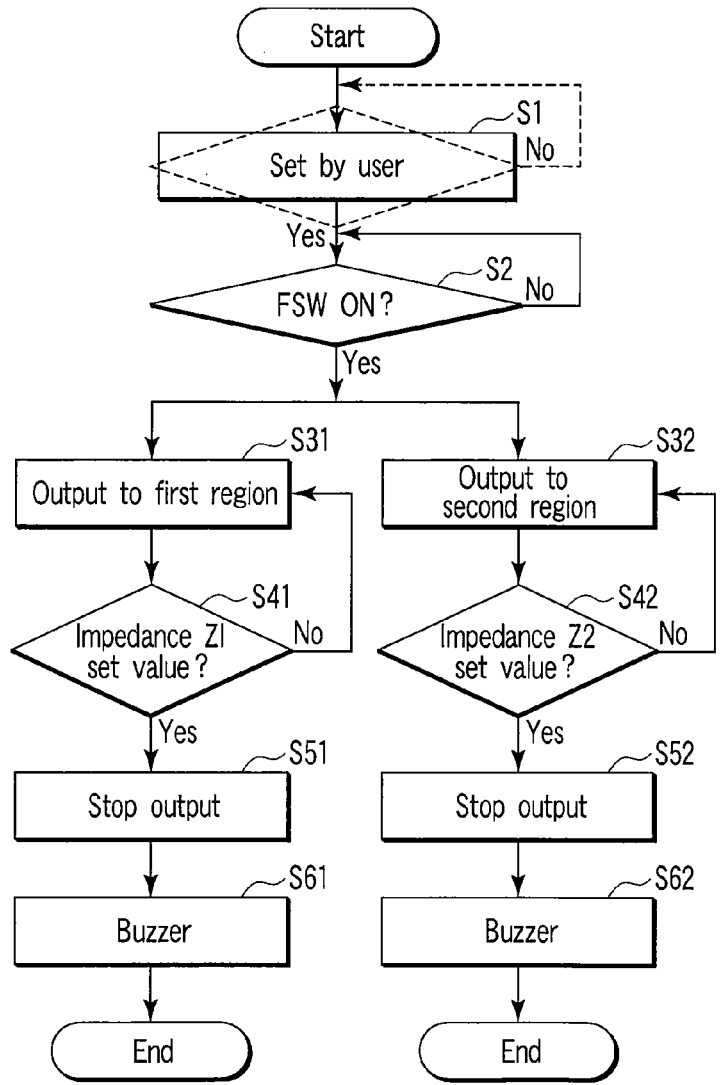
FIG. 5 is a schematic flowchart when the treatment system according to the first embodiment is used to give a treatment using radio-frequency energy to a living tissue.

FIG. 5 shows an example of a control flow of the surgical instrument 12 by the first radio-frequency energy output circuit 104 and the second radio-frequency energy output circuit 106. FIG. 6A is a graph showing a relationship between an output from the first radio-frequency energy output circuit 104 and a time and a relationship between an output from the second radio-frequency energy output circuit 106 and a time. FIG. 6B shows a schematic displacement of the impedance Z usually measured when energy is input as depicted in FIG. 6A with respect to a time.

An operator operates the display section 108 in the energy source 14 to set output conditions for the treatment system 10 in advance (STEP 1). Specifically, he/she sets outputs (set powers P1set [W] and P2set [W]) from the first radio-frequency energy output circuit 104 and the second radio-frequency energy output circuit 106, threshold values Z1 and Z2 of the impedance Z of the living tissue $L_T$, and others. Here, a description will be given on the assumption that the output from the first radio-frequency energy output circuit 104 (the set power P1set) is set larger than the output from the second radio-frequency energy circuit 106 (the set power P2set).

Incidentally, in regard to setting the output conditions for the treatment system 10, it is also preferable to form a flow depicted in FIG. 5 to again set the output conditions after the pedal 16a of the footswitch 16 is pressed once and a treatment is thereby terminated.

In a state where the second holding member 64 is closed with respect to the first holding member 62 as shown in FIG. 2A, the holding portion 26 and the shaft 24 of the surgical instrument 12 are inserted into an abdominal cavity through an abdominal wall. The holding portion 26 of the surgical instrument 12 is set to face the living tissue $L_T$ as a treatment target.

The holding portion opening/closing knob 32 of the handle 22 is operated to hold the living tissue $L_T$ as the treatment target by the first holding member 62 and the second holding member 64. At this time, the sheath 44 is moved toward the proximal end portion of the shaft 24 with respect to the cylindrical body 42. The base portions 74 and 84 cannot be maintained in a cylinder because of the urging force of the elastic member 92a, and the second holding member 64 is thereby opened with respect to the first holding member 62.

The living tissue $L_T$ as the treatment target is arranged between the first continuous electrode 76 of the first holding member 62 and the second continuous electrode 86 of the second holding member 64 and between the first discrete electrodes 78 of the first holding member 62 and the second discrete electrodes 88 of the second holding member 64. In this state, the grasping portion opening/closing knob 32 of the handle 22 is operated. At this time, the sheath 44 is moved toward the distal end portion of the shaft 24 with respect to the cylindrical body 42. The base portions 74 and 84 are closed to be formed into a cylinder by the sheath 44 against the urging force of the elastic member 92a. Therefore, the main body 72 of the first holding member 62 formed integrally with the base portion 74 and the main body 82 of the second holding member 64 formed integrally with the base portion 84 are closed. That is, the second holding member 64 is closed with respect to the first holding member 62. In this manner, the living tissue $L_T$ as the treatment target is grasped between the first holding member 62 and the second holding member 64.

At this time, the living tissue $L_T$ as the treatment target is in contact with both the first continuous electrode 76 of the first holding member 62 and the second continuous electrode 86 of the second holding member 64. The living tissue $L_T$ as the treatment target is in contact with both the first discrete electrodes 78 of the first holding member 62 and the second discrete electrodes 88 of the second holding member 64. A peripheral tissue of the living tissue $L_T$ as the treatment target is appressed against both the opposed contact surfaces of the edge portion of the holding surface 72b of the first holding member 62 and the edge portion (not shown) of the holding surface 82b of the second holding member 64.

The pedal 16a of the footswitch 16 is operated in a state where the living tissue is grasped between the first holding member 62 and the second holding member 64 in this manner. The control section 102 in the energy source 14 determines whether the pedal 16a of the switch 16 has been pressed by the operator to be turned on (STEP 2).

When it is determined that the pedal 16a of the switch 16 has been pressed to be turned on, radio-frequency energy is supplied from the first radio-frequency energy output circuit 104 in the energy source 14 to the living tissue $L_T$ between the first continuous electrode 76 and the second continuous electrode 86 (the living tissue in a first region) (STEP 31). At the same time, radio-frequency energy is supplied from the second radio-frequency energy output circuit 106 in the energy source 14 to the living tissue $L_T$ between the first discrete electrodes 78 and the second discrete electrodes 88 (the living tissue in a second region) (STEP 32).

Moreover, the first radio-frequency energy output circuit 104 supplies the set power P1set [W] preset in the display section 108, e.g., a power of approximately 20 [W] to 80 [W] to the living tissue $L_T$ between the first continuous electrode 76 of the first holding member 62 and the second continuous electrode 86 of the second holding member 64.

Therefore, the first radio-frequency energy output circuit 104 energizes the living tissue $L_T$ as the treatment target between the first continuous electrode 76 of the first holding member 62 and the second continuous electrode 86 of the second holding member 64 with a radio-frequency current. That is, the radio-frequency energy is supplied to the living tissue $L_T$ grasped between the electrodes 76 and 86. Therefore, Joule heat is generated in the living tissue $L_T$ grasped between the electrodes 76 and 86 to heat the living tissue $L_T$ itself. A function of the Joule heat destroys cell membranes in the living tissue $L_T$ held between the electrodes 76 and 86 to discharge a material in the cell membranes, thereby homogenizing the living tissue with extracellular components including collagen and others. Since the radio-frequency current is flowed through the living tissue $L_T$ between the electrodes 76 and 86, further Joule heat functions with respect to the thus homogenized tissue $L_T$, and joining surface of the living tissue or layers of the tissue are joined, for example. Therefore, when the living tissue $L_T$ between the electrodes 76 and 86 is energized with the radio-frequency current, the living tissue $L_T$ itself generates heat and the inside of the living tissue $L_T$ is denatured (the living tissue $L_T$ is cauterized) while dehydrating. Accordingly, the living tissue $L_T$ is continuously (a substantially U-shaped state) denatured by the first continuous electrode 76 and the second continuous electrode 86.

At this time, the impedance Z of the grasped living tissue $L_T$ is measured by the radio-frequency energy output circuit 104 through the first continuous electrode 76 and the second continuous electrode 86. An impedance Z0 at the time of start of a treatment is, e.g., approximately 60[Ω] as shown in FIG. 6B. Additionally, a value of the impedance is increased as the radio-frequency current flows through the living tissue $L_T$ and the living tissue $L_T$ is cauterized.

A fluid (e.g., a liquid (blood) and/or a gas (steam)) is discharged from the living tissue $L_T$ as the living tissue $L_T$ is cauterized. At this time, the holding surface 72b of the first holding member 62 and the holding surface 82b of the second holding member 64 are appressed against the living tissue $L_T$ as compared with the first continuous electrode 76 and the second continuous electrode 86. Therefore, each of the holding surfaces 72b and 82b functions as a barrier portion (a dam) that suppresses the fluid from flowing toward the outside of the first holding member 62 and the second holding member 64. Therefore, the fluid discharged from the living tissue $L_T$ is flowed into the cutter guide groove 62a on the inner side of the first continuous electrode 76 and the cutter guide groove 64a on the inner side of the second continuous electrode 86, and flowed through the shaft 24 from the first holding member 62 and the second holding member 64 based on, e.g., suction. The fluid is continuously flowed into the cutter guide grooves 62a and 64a while the fluid is discharged from the living tissue $L_T$. Therefore, it is possible to avoid the occurrence of thermal spread due to the fluid discharged from the living tissue $L_T$ in a high-temperature state and also prevent portions that are not the treatment target from being affected.

Then, the control section 102 determines whether the impedance Z at the time of output of the radio-frequency energy calculated based on a signal from the radio-frequency energy output circuit 104 has become equal to or above the threshold value Z1 (which is approximately 1000[Ω] in this example as shown in FIG. 6B) preset (STEP 1) in the display section 108 (STEP 41). The threshold value Z1 is provided at a position where a previously known increase rate of a value of the impedance Z blunts. Furthermore, when it is determined that the impedance Z is smaller than the threshold value Z1, the processing returns to STEP 31. That is, the radio-frequency energy for the treatment is kept being supplied to the living tissue $L_T$ grasped between the first continuous electrode 76 of the first holding member 62 and the second continuous electrode 86 of the second holding member 64.

When it is determined that the impedance Z is larger than the threshold value Z1, the control section 102 transmits a signal to the first radio-frequency energy output circuit 104. Moreover, an output from the first radio-frequency energy output circuit 104 to the first continuous electrode 76 and the second continuous electrode 86 is stopped (STEP 51).

After stopping the output, the control section 102 produces buzzer sound from the speaker 110 (STEP 61). In this manner, termination of the treatment for the living tissue $L_T$ carried out from the first radio-frequency energy output circuit 104 through the first continuous electrode 76 and the second continuous electrode 86 can be readily recognized.

On the other hand, as explained above, the second radio-frequency energy output circuit 106 in the energy source 14 supplies the energy to the living tissue (the living tissue in the second region) $L_T$ between the first discrete electrodes 78 and the second discrete electrodes 88 (STEP 32).

Further, the second radio-frequency energy output circuit 106 supplies the set power P2set [W] preset in the display section 108, e.g., a power of approximately 20 [W] to 80 [W] to the living tissue $L_T$ between the first discrete electrodes 78 of the first holding member 62 and the second discrete electrodes 88 of the second holding member 64. It is to be noted that the output from the second radio-frequency energy output circuit 106 to the first discrete electrodes 78 and the second discrete electrodes 88 may be smaller than the output from the first radio-frequency energy output circuit 104 to the first continuous electrode 76 and the second continuous electrode 86. Such magnitudes of the outputs are appropriately set before the treatment in accordance with, e.g., a target or an object of the treatment (STEP 1).

Therefore, the radio-frequency current flows through the living tissue $L_T$ grasped between the first holding member 62 and the second holding member 64, and heat is generated in the living tissue $L_T$ by the function of Joule heat to start cauterization of the tissue (denaturalization of the tissue). Then, the first discrete electrodes 78 and the second discrete electrodes 88 discretely denature the living tissue $L_T$ between these discrete electrodes 78 and 88. At this time, the impedance Z of the grasped living tissue $L_T$ is measured by the second radio-frequency energy output circuit 106 through the first discrete electrodes 78 and the second discrete electrodes 88. An impedance Z0 at the start of the treatment is, e.g., approximately 60[Ω] as shown in FIG. 6B. Moreover, a value of the impedance Z is increased as the radio-frequency current flows through the living tissue $L_T$ and the living tissue $L_T$ is thereby cauterized.

In this manner, a fluid (e.g., a liquid [blood] and/or a gas [steam]) is discharged from the living tissue $L_T$ as the living tissue $L_T$ is cauterized. At this time, an adhesion degree of the holding surface 72b of the first holding member 62 and the holding surface 82b of the second holding member 64 with respect to the living tissue $L_T$ is higher than that of the first discrete electrodes 78 and the second discrete electrodes 88. Therefore, each of the holding surfaces 72b and 82b functions as a barrier portion (a dam) that suppresses the fluid from flowing to the outside of the first holding member 62 and the second holding member 64. Accordingly, the fluid discharged from the living tissue $L_T$ is flowed into the cutter guide grooves 62a and 64a on the inner side of the first continuous electrode 76 provided on the inner side of the first discrete electrodes 78 and on the inner side of the second continuous electrode 86 provided on the inner side of the second discrete electrodes 88, and further flowed through the shaft 24 from the first and second holding members 62 and 64 based on, e.g., suction. The fluid is kept being flowed into the cutter guide grooves 62a and 64a while the fluid is discharged from the living tissue $L_T$. Therefore, it is possible to avoid the occurrence of thermal spread due to the fluid discharged from the living tissue $L_T$ in a high temperature state and prevent parts that are not treatment targets from being affected.

Then, the control section 102 determines whether the impedance Z at the time of outputting the radio-frequency energy calculated based on the signal from the second radio-frequency energy output circuit 106 has become equal to or above the preset threshold value Z2 (which is approximately 1000[Ω] in this example as shown in FIG. 6B) (STEP 42). It is preferable for the threshold value Z2 to be set to a position where a previously known increase rate of a value of the impedance Z blunts. Additionally, when it is determined that the impedance Z is smaller than the threshold value Z2, the processing returns to STEP 32. That is, the radio-frequency energy for the treatment is kept being supplied to the living tissue $L_T$ held between the first discrete electrodes 78 of the first holding member 62 and the second discrete electrodes 88 of the second holding member 64.

When it is determined that the impedance Z is higher than the threshold value Z2, the control section 102 transmits a signal to the second radio-frequency energy output circuit 106. Further, the output from the second radio-frequency energy output circuit 106 to the first discrete electrodes 78 and the second discrete electrodes 88 is stopped (STEP 52).

Furthermore, after stopping the output, the control section 102 produces buzzer sound from the speaker 110 (STEP 62). In this manner, termination of the treatment for the living tissue $L_T$ carried out from the second radio-frequency energy output circuit 106 through the first discrete electrodes 78 and the second discrete electrodes 88 can be easily recognized. At this time, it is preferable for the buzzer sound produced when the output from the second radio-frequency energy output circuit 106 is stopped to be sound that can be recognized as different from the buzzer sound produced when the output from the first radio-frequency energy output circuit 104 is stopped. Moreover, it is preferable that in the case of the outputs from the first radio-frequency energy output circuit 104 and the second radio-frequency energy output circuit 106 are substantially simultaneously stopped, the buzzer sound produced when the output from the first radio-frequency energy output circuit 104 is stopped, are different from the buzzer sound produced when the output from the second radio-frequency energy output circuit 106 is stopped, and the both buzzer sound can be heard due to time shifting.

It is to be noted that the treatment is carried out from "Start" to "End" depicted in FIG. 5 while the pedal 16a of the footswitch 16 is kept in the pressed state. However, when the pedal 16a is released from the pressed state in the process from "Start" to "End", the treatment is forcibly stopped by the control section 102 at a time point where the pedal 16a is released. That is, when the pedal 16a is released from being pressed, the control section 102 stops both the outputs from the first radio-frequency energy output circuit 104 and the second radio-frequency energy output circuit 106.

Further, as shown in FIG. 6C, the output (the set power P1set) from the first radio-frequency energy output circuit 104 may be set in the state depicted in FIG. 6A, and the output (the set power P2set) from the second radio-frequency energy output circuit 106 may be turned on/off in a square waveform at predetermined intervals.

Furthermore, as shown in FIG. 6D, the output (the set power P1set) from the first radio-frequency energy output circuit 104 may be set in the state depicted in FIG. 6A, and the output (the set power P2set) from the second radio-frequency energy output circuit 106 may be turned on/off in a pulse waveform at predetermined intervals.

Moreover, when terminating the treatment, supply of the energy may be set to be stopped based on elapse of a set time t at STEP 1 irrespective of whether the impedance Z has reached the threshold value Z1 or Z2.

Additionally, although not shown, it is also preferable to appropriately set not only the output from the second radio-frequency energy output circuit 106 but also the output from the first radio-frequency energy output circuit 104 to the square waveform or the pulse waveform depicted in FIG. 6C or 6D.

Figure 7A:
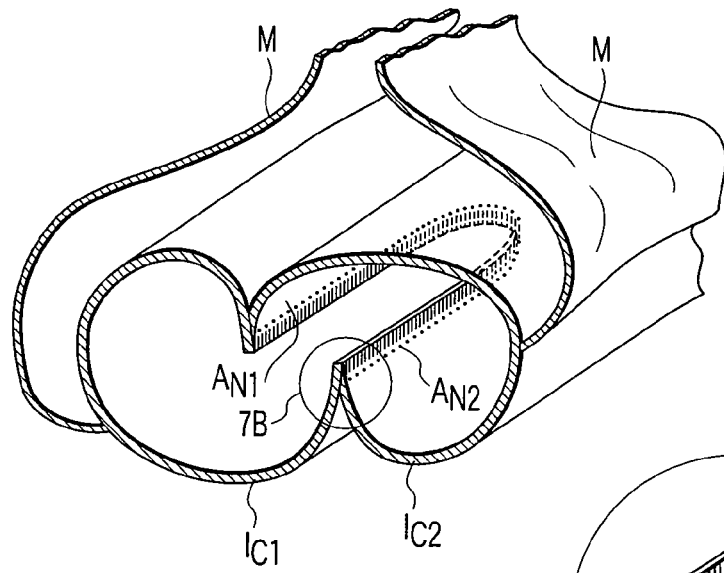
FIG. 7A is a schematic perspective view showing a state where two intestinal canals of a small intestine are anastomosed and also a schematic view taken along a line 7A-7A depicted in FIG. 7C which will be explained later.
Figure 7B:
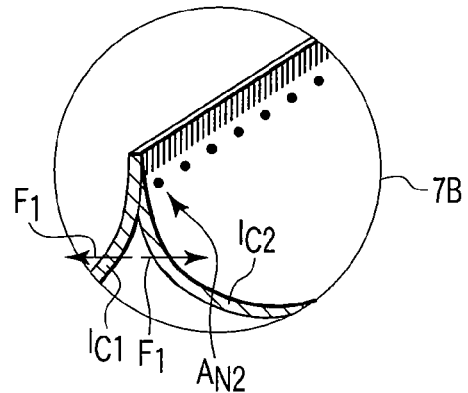
FIG. 7B is an enlarged schematic view of a part denoted by reference character 7B in FIG. 7A.
Figure 7C:
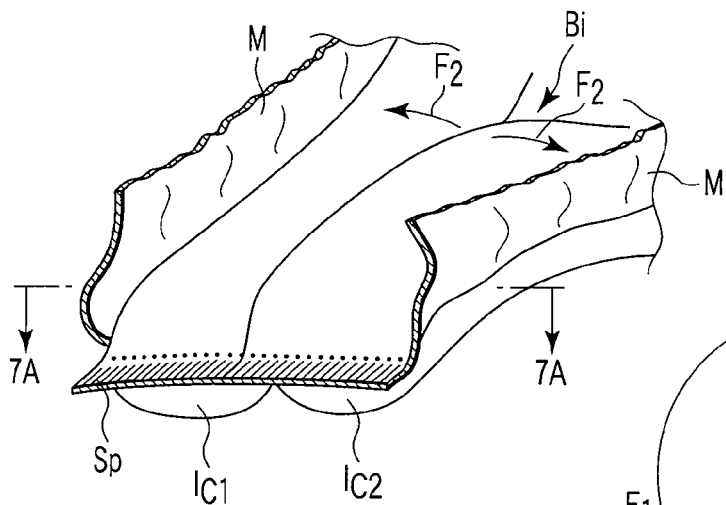
FIG. 7C is a schematic view showing a state where end portions of the two intestinal canals of the small intestine are sealed after anastomosing these intestinal canals.
Figure 7D:
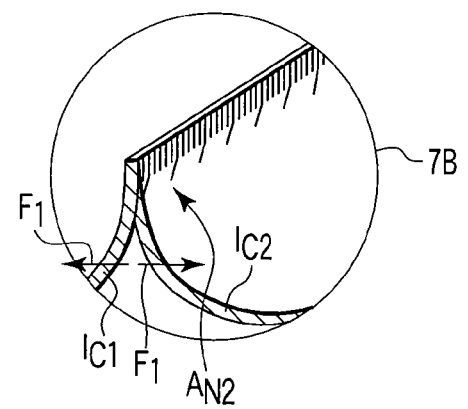
FIG. 7D is an enlarged schematic view showing a part designated by reference character 7B in FIG. 7A as a modification of FIG. 7B.

A description will now be given as to an example where the treatment system 10 having such a function is used to join, e.g., intestinal canals $I_{C1}$ and $I_{C2}$ provided in parallel in a small intestine and seal the joined intestinal canals $I_{C1}$ and $I_{C2}$ as shown in FIGS. 7A to 7C.

The display section 108 in the energy source 14 is operated to previously set outputs from the first radio-frequency energy output circuit 104 and the second radio-frequency energy output circuit 106. At this time, since the pair of intestinal canals $I_{C1}$ and $I_{C2}$ arranged in parallel are to be joined, the output from the second radio-frequency energy output circuit 106 is appropriately set high.

The pair of intestinal canals $I_{C1}$ and $I_{C2}$ arranged in parallel are held by the holding surface 72b of the first holding member 62 and the holding surface 82b of the second holding member 64 to sandwich wall surfaces of both the intestinal canals $I_{C1}$ and $I_{C2}$.

In this state, when the pedal 16a of the footswitch 16 is pressed, the energy is supplied to the living tissues $L_T$ between the first continuous electrode 76 and the second continuous electrode 86 and between the first discrete electrodes 78 and the second discrete electrodes 88. Therefore, the first continuous electrode 76, the second continuous electrode 86, the first discrete electrodes 78, and the second discrete electrodes 88 heat and denature the intestinal canals $I_{C1}$ and $I_{C2}$.

Further, the output from the first radio-frequency energy output circuit 104 is stopped when the living tissue $L_T$ between the first continuous electrode 76 and the second continuous electrode 86 has reached the predetermined threshold value Z1, and the output from the second radio-frequency energy output circuit 106 is stopped when the living tissues $L_T$ between the first discrete electrodes 78 and the second discrete electrodes 88 has reached the predetermined threshold value Z2.

When the impedance Z of the living tissues $L_T$ between the first continuous electrode 76 and the second continuous electrode 86 has reached the predetermined threshold value Z1, the first continuous electrode 76 and the second continuous electrode 86 heat and denature the intestinal canals $I_{C1}$ and $I_{C2}$ to be joined. When the impedance Z of the living tissues $L_T$ between the first discrete electrodes 78 and the second discrete electrodes 88 has reached the predetermined threshold value Z2, the first discrete electrodes 78 and the second discrete electrodes 88 heat and denature the intestinal canals $I_{C1}$ and $I_{C2}$ to be joined. In this manner, the intestinal canals $I_{C1}$ and $I_{C2}$ are continuously and discretely denatured and joined (anastomosed).

Further, the cutter driving knob 34 depicted in FIG. 1A is operated to advance the cutter 54 along the cutter guide grooves 62a and 64a from the state depicted in FIGS. 2A and 2B while keeping holding the intestinal canals $I_{C1}$ and $I_{C2}$ between the first holding member 62 and the second holding member 64. The blade 54a at the distal end of the cutter 54 cuts the inner side of a region denatured and joined by the first continuous electrode 76 and the second continuous electrode 86 as the cutter 54 moves forward. Furthermore, the cutter 54 cuts the inner side of a region denatured into substantially a U-shape by the first continuous electrode 76 and the second continuous electrode 86 until reaching a position near a distal end of the region. Therefore, as shown in FIG. 7A, portions of wall surfaces of the intestinal canals $I_{C1}$ and $I_{C2}$ sealed into substantially a U-shape is cut at the center, thereby allowing the wall surfaces of the intestinal canales $I_{C1}$ and $I_{C2}$ to communicate with each other.

In this state, the cutter driving knob 34 is operated to retract the cutter 54. Thereafter, the holding portion opening/closing knob 32 of the handle 22 is operated to open the first and second holding members 62 and 64. At this time, a first anastomosed portion $A_{N1}$ on a mesentery M side and a second anastomosed portion $A_{N2}$ on a side opposed to the mesentery M side are formed. For example, as shown in FIG. 7B, a continuously joined outer portion of each of the first anastomosed portion $A_{N1}$ and the second anastomosed portion $A_{N2}$ is discretely denatured. At this time, as explained above, since the output supplied to the first discrete electrodes 78 and the second discrete electrodes 88 from the second radio-frequency energy output circuit 106 has been set high, the discretely natured and joined portions are firmly joined, and hence they have peeling resistance.

Moreover, the display section 108 in the energy source 14 is again operated to set the output from the first radio-frequency energy output circuit 104 high in accordance with the treatment target (sealing of the intestinal canals $I_{C1}$ and $I_{C2}$).

The first holding member 62 and the second holding member 64 are closed to hold end portions of the intestinal canals $I_{C1}$ and $I_{C2}$. In this state, the pedal 16a of the footswitch 16 is pressed to supply the energy to the first continuous electrode 76 and the second continuous electrode 86 from the first radio-frequency energy output circuit and also supply the energy to the first discrete electrodes 78 and the second discrete electrodes 88 from the second radio-frequency energy output circuit 106. Therefore, the end portions of the intestinal canals $I_{C1}$ and $I_{C2}$ are joined by the first continuous electrode 76 and the second continuous electrode 86 to form a sealed portion $S_P$, and the first discrete electrodes 78 and the second discrete electrodes 78 are used to discretely join these end portions.

Therefore, as shown in FIG. 7C, the end portions of the intestinal canals $I_{C1}$ and $I_{C2}$ are denatured and sealed by the first continuous electrode 76 and the second continuous electrode 86. That is, the sealed portion $S_P$ is formed at the end portions of the intestinal canals $I_{C1}$ and $I_{C2}$. At this time, a cross section taken along a line 7A-7A in FIG. 7C is generally in such as state as depicted in FIG. 7A. Therefore, the intestinal canals $I_{C1}$ and $I_{C2}$ are anastomosed in a state where the end portions are sealed at the sealed portion $S_P$.

It is to be noted that an unnecessary region of the sealed portion $S_P$ is cut off by, e.g., the cutter 54. At this time, continuously joined peripheral parts of the sealed end portions (the sealed portion $S_P$) of the intestinal canals $I_{C1}$ and $I_{C2}$ are likewise discretely denatured like the state shown in FIG. 7B. That is, in the intestinal canals $I_{C1}$ and $I_{C2}$, the living tissues between the regions denatured and joined by the first discrete electrodes 78 and the second discrete electrodes 88 are not denatured. Therefore, a periphery (a vicinity) of a part where the living tissues are joined by the first discrete electrodes 78 and the second discrete electrodes 88 is in a state where the living tissues of the non-denatured intestinal canals $I_{C1}$ and $I_{C2}$ are in contact with (appressed against) each other.

Therefore, in the first anastomosed portion $A_{N1}$ on the mesentery M side, a force acts in a direction along which the intestinal canals $I_{C1}$ and $I_{C2}$ are appressed against each other. Then, a region where the living tissues have been denatured by the first discrete electrodes 78 and the second discrete electrodes 88 exercises a force to further assuredly press the living tissues against each other. Additionally, in the second anastomosed portion $A_{N2}$ on the side opposed to mesentery M side, a force $F_1$ acts in a direction along which the intestinal canals $I_{C1}$ and $I_{C2}$ are opened, but a region where the living tissues have been denatured by the first discrete electrodes 78 and the second discrete electrodes 88 exercises a force to press the living tissues against each other. Therefore, a mutual network of the non-denatured living tissues of the intestinal canals $I_{C1}$ and $I_{C2}$ is produced, and a tissue regeneration force for the living tissues is demonstrated, thereby regenerating the living tissues of the intestinal canals $I_{C1}$ and $I_{C2}$ on an earlier stage.

As explained above, according to this embodiment, the following effects can be obtained.

Since the first continuous electrode 76 and the first discrete electrodes 78 are separately arranged in the first holding member 62 and the second continuous electrode 86 and the second discrete electrodes 88 are separately arranged in the second holding member 64, the output from the first radio-frequency energy output circuit 104 to the first continuous electrode 76 and the second continuous electrode 86 and the output from the second radio-frequency energy output circuit 106 to the first discrete electrodes 78 and the second discrete electrodes 88 can be separately set. Therefore, since the outputs from the first radio-frequency energy output circuit 104 and the second radio-frequency energy output circuit 106 can be respectively set in accordance with each treatment, it is possible to readily cope with various kinds of treatments, thereby expanding general versatility of the treatments. That is, just operating the display section 108 to change the settings enables optimally setting the surgical instrument 12 in accordance with various applications to carry out each treatment.

As explained above, the first continuous electrode 76 and the first discrete electrodes 78 are arranged on the holding surface 72b of the first holding member 62, and the second continuous electrode 86 and the second discrete electrodes 88 are arranged on the holding surface 82b of the second holding member 64. Therefore, living tissues (e.g., the intestinal canals $I_{C1}$ and $I_{C2}$) between the first continuous electrode 76 of the first holding member 62 and the second continuous electrode 86 of the second holding member 64 can be heated, denatured, and continuously joined. Therefore, a treatment can be carried out in an optimum state. For example, the output from the second radio-frequency energy output circuit 106 is increased when joining, e.g., tubular living tissues, and the output from the first radio-frequency energy output circuit 104 is increased when sealing living tissues.

At this time, for example, as shown in FIG. 7B, the region where the living tissues are continuously denatured to be joined and the region where the living tissues are discretely natured to be joined are close to each other. Furthermore, non-denatured portions are present between the living tissues around the region where the living tissues are discretely denatured to be joined. Therefore, the non-denatured living tissues around the region where the living tissues are denatured to be joined can be maintained in a state where the living tissues are in contact with (appressed against) each other. That is, the first discrete electrodes 78 and the second discrete electrodes 88 play a great role of maintaining the living tissues to which the force $F_1$ in a separating direction is applied in the state where they are appressed against each other, for example.

When anastomosing, e.g., the two intestinal canals $I_{C1}$ and $I_{C2}$, the force $F_1$ acts in the direction along which the intestinal canals $I_{C1}$ and $I_{C2}$ are separated from each other on the opposite side of the mesentery M side shown in FIGS. 7A and 7C. However, since the intestinal canals $I_{C1}$ and $I_{C2}$ are discretely joined by the first discrete electrodes 78 and the second discrete electrodes 88, the intestinal canals $I_{C1}$ and $I_{C2}$ can be discretely joined. Therefore, the intestinal canals $I_{C1}$ and $I_{C2}$ can be maintained in an appressed state.

Accordingly, the region of the living tissues joined by the first discrete electrodes 78 and the second discrete electrodes 88 plays a role of maintaining a state where the living tissues are attracted to and appressed against each other. That is, the region of the living tissues joined by the first discrete electrodes 78 and the second discrete electrodes 88 plays a role of maintaining adherence of living bodies. Therefore, a mutual network of the living tissues which are appressed against (adhere to) each other can be produced, and a tissue regeneration force for the living tissues can be readily demonstrated, thus regenerating the living tissues on an earlier stage.

It is to be noted that the description has been given as to the example where the first discrete electrodes 78 of the first holding member 62 are arranged at substantially equal intervals and have substantially equal areas in this embodiment. However, it is also preferable that intervals between the discrete electrodes 78 adjacent to each other are different or areas of the discrete electrodes 78 are different. When tissues are discretely treated by the discrete electrodes 78, a region that has come into contact with the discrete electrodes 78 is denatured. However, the discrete electrodes 78 can be changed in many ways as long as the living tissues can be maintained in a state where they are in contact with each other without partially denaturing the living tissues between the discrete electrodes 78 and the discrete electrodes 78 adjacent thereto. Of course, this can be likewise applied to the second discrete electrodes 88 of the second holding member 64.

Further, it is also preferable to change the plurality of first discrete electrodes 78 of the first holding member 62 and the plurality of second discrete electrodes 88 of the second holding member 64 to respective heaters (heat generating elements) or change the first continuous electrode 76 of the first holding member 62 and the second continuous electrode 86 of the second continuous electrode 86 to the heaters (the heat generating elements). Alternatively, it is also preferable to change both the plurality of first and second discrete electrodes 78 and 88 of the first and second holding members 62 and 64 and the first and second continuous electrodes 76 and 86 of the first and second holding members 62 and 64 to the heaters. Furthermore, a heater 120 can be arranged on a back surface of the electrodes to carry out a treatment using radio-frequency energy and thermal energy so that heat can be conducted from the heater 120 to the electrodes to give the treatment to the living tissues (see FIG. 3D). When using the heater 120, for example, the first radio-frequency energy output circuit 104 of the energy source 14 is used as a circuit that supplies energy to the heater 120.

Moreover, although the example where the cutter 54 is provided has been explained in this embodiment, the cutter 54 may not be provided depending on a treatment target. When the cutter 54 is not provided, the cutter guide grooves 62a and 64a can function as fluid discharge grooves (flow paths) through which a fluid, e.g., steam or a liquid generated from the living tissues is led to the handle 22 side of the energy treatment instrument 12.

Figure 3D:
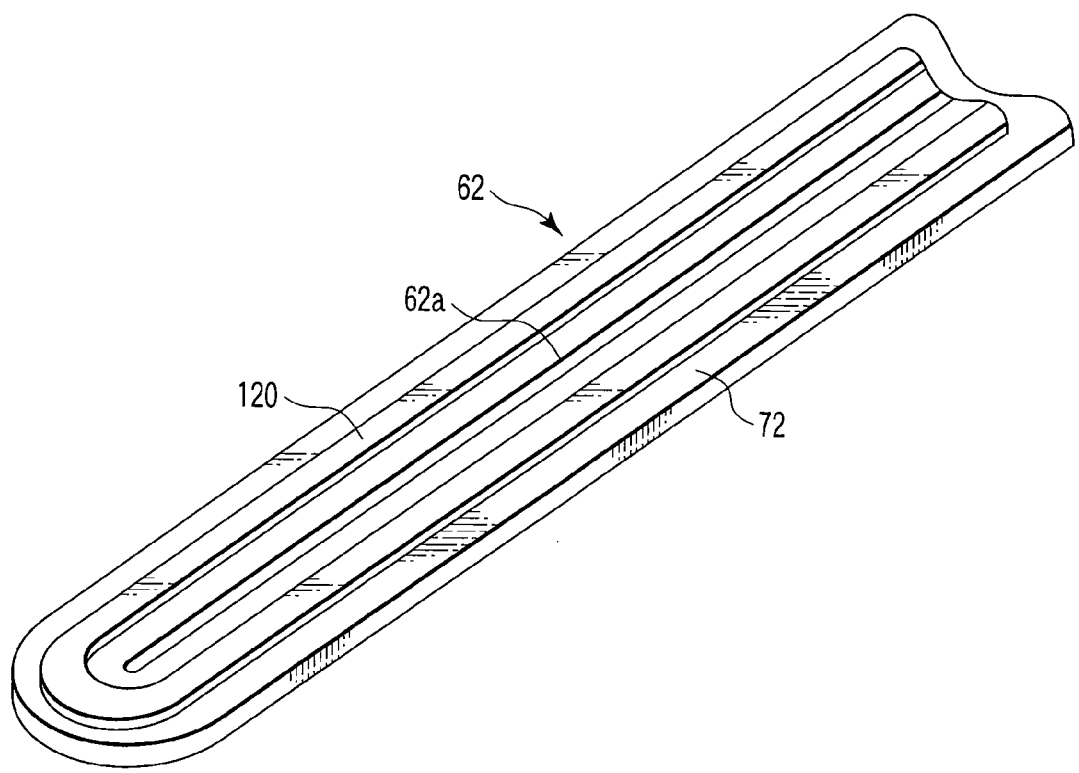
FIG. 3D is a schematic plan view showing a back surface of an electrode arranged in a main body of the first holding member on the side close to the second holding member in the holding portion of the energy treatment instrument in the treatment system according to the first embodiment.
Figure 3E:
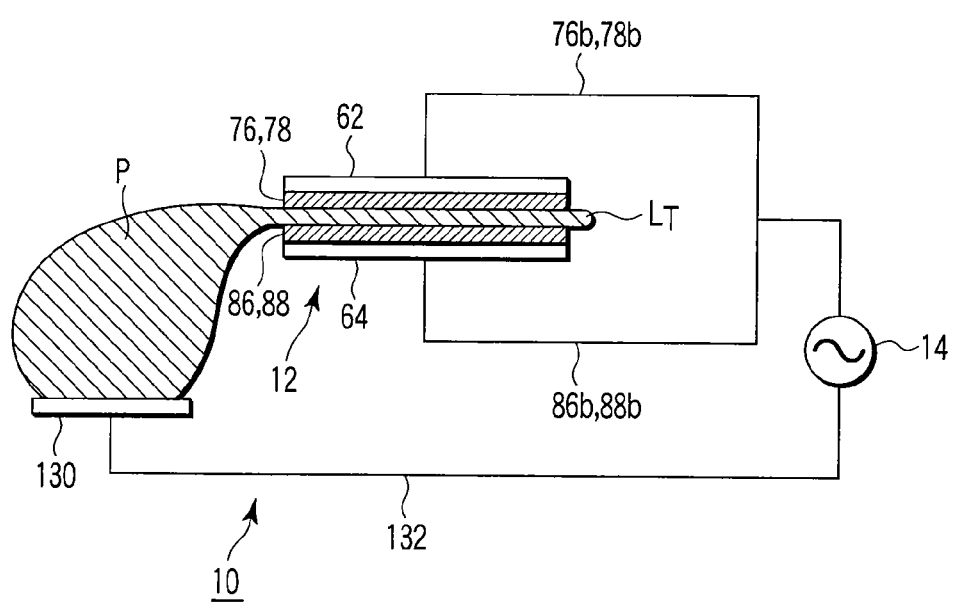
FIG. 3E is a schematic view when the surgical instrument in the treatment system according to the first embodiment supplies monopolar type radio-frequency energy to treat a living tissue.

Here, as shown in FIG. 1B, the description has been given as to the example where the surgical instrument 12 that has the electrodes having different potentials (a potential between the first continuous electrode 76 and the second continuous electrode 86 and a potential between the first discrete electrodes 78 and the second discrete electrodes 88) in the first holding member 62 and the second holding member 64 and gives the bipolar type radio-frequency energy treatment. However, as shown in FIG. 3E, using a surgical instrument that gives a monopolar type radio-frequency energy treatment is also preferable. In this case, a counter electrode plate 130 is attached to a patient P as a treatment target. The counter electrode plate 130 is connected with the energy source 14 through an energization line 132. Moreover, the first continuous electrode 76 of the first holding member 62 and the second continuous electrode 86 of the second holding member 64 is in an equal potential state where the first electrode energization line 76b is electrically connected with the third electrode energization line 86b. Additionally, the first discrete electrodes 78 of the first holding member 62 and the second discrete electrodes 88 of the second holding member 64 is in an equal potential state where the second electrode energization line 78b is electrically connected with the fourth electrode energization line 88b. In such cases, since areas of the living tissues $L_T$ that are in contact with the continuous electrodes 76 and 86 and the discrete electrodes 78 and 88 are respectively small, a current density is high, but a current density of the counter electrode plate 130 is reduced. Therefore, the living tissue $L_T$ that is grasped by the first holding member 62 and the second holding member 64 is heated, whereas heating of the living tissue $L_T$ that is in contact with the counter electrode plate 130 is negligibly small. Accordingly, of the portion grasped by the first holding member 62 and the second holding member 64, the living tissue $L_T$ that is in contact with the continuous electrodes 76 and 86 and the discrete electrodes 78 and 88 alone is heated and denatured.

Furthermore, although not shown, when using the monopolar type surgical instrument, it is also preferable to provide the electrodes in one of the first holding member 62 and the second holding member 64.

Moreover, although the example of using the two radio-frequency energy output circuits 104 and 106 has been explained in this embodiment, the number of the radio-frequency energy output circuits is not restricted to two, and three or four circuits can be appropriately used in accordance with a treatment, for example. That is, at the time of a treatment, finer settings can be provided in the display section 108, thereby optimizing a treatment.

[First Modification of First Embodiment]

A first modification will now be explained with reference to FIGS. 8 to 9C.

FIG. 8 shows an example of a control flow of the surgical instrument 12 by the first radio-frequency energy output circuit 104 and the second radio-frequency energy output 106. FIG. 9A is a graph showing a relationship between an output from the first radio-frequency energy output circuit 104 and a time and a relationship between an output from the second radio-frequency energy output circuit 106 and a time.

An operator previously operates the display section 108 of the energy source 14 to set output conditions for the treatment system 10 (STEP 101). Specifically, outputs (set powers P1set [W] and P2set [W]) from the first radio-frequency energy output circuit 104 and the second radio-frequency energy output circuit 106, threshold values Z1 and Z2 of the impedance Z of the living tissue $L_T$, and others are set. Here, as shown in FIG. 9A, a description will be given as to an example where the output (the set power P1set) from the first radio-frequency energy output circuit 104 is set higher than the output (the set power P2set) from the second radio-frequency energy output circuit 106.

The pedal 16a of the footswitch 16 is operated in a state where the living tissue is grasped between the first holding member 62 and the second holding member 64. The control section 102 of the energy source 14 determines whether the footswitch pedal 16a of the switch 16 has been pressed by the operator according to whether the switch 16 has been turned on (STEP 102).

When the switch 16 is turned on, the first radio-frequency energy output circuit 104 in the energy source 14 supplies energy to the living tissue (the living tissue in a first region) $L_T$ between the first continuous electrode 76 and the second continuous electrode 86 through the cable 28 (STEP 103). Additionally, the first radio-frequency energy output circuit 104 supplies the set power P1set [W] previously set in the display section 108, e.g., a power of approximately 20 [W] to 80 [W] to the living tissue $L_T$ between the first continuous electrode 76 of the first holding member 62 and the second continuous electrode 86 of the second holding member 64. It is to be noted that, in this modification, the first radio-frequency energy output circuit 104 is allowed to relatively slowly reach the set power P1set [W] as shown in FIG. 9A.

Therefore, the first radio-frequency energy output circuit 104 energizes the living tissue $L_T$ as a treatment target between the first continuous electrode 76 of the first holding member 62 and the second continuous electrode 86 of the second holding member 64 with a radio-frequency current. That is, the radio-frequency energy is supplied to the living tissue $L_T$ grasped between the electrodes 76 and 86. Therefore, the living tissue $L_T$ is continuously (a substantially U-shaped state) is denatured by the first continuous electrode 76 and the second continuous electrode 86.

At this time, the impedance Z of the grasped living tissue $L_T$ is measured by the radio-frequency energy output circuit 104 through the first continuous electrode 76 and the second continuous electrode 86. An impedance Z0 at the start of a treatment is, e.g., approximately 60[Ω] as shown in FIG. 6B. Furthermore, a value of the impedance Z is increased as the radio-frequency current is flowed through the living tissue $L_T$ and the living tissue $L_T$ is cauterized.

Then, the control section 102 determines whether the impedance Z at the time of output of the radio-frequency energy calculated based on a signal from the radio-frequency energy output circuit 104 has become equal to or above the threshold value Z1 previously set (STEP 101) in the display section 108 (STEP 104). The threshold value Z1 is provided at a position where a previously known increasing rate of the value of the impedance Z blunts. Moreover, when it is determined that the impedance Z is smaller than the threshold value Z1, the processing returns to STEP 103. That is, the radio-frequency energy for a treatment is kept being supplied to the living tissue $L_T$ grasped between the first continuous electrode 76 of the first holding member 62 and the second continuous electrode 86 of the second holding member 64.

When it is determined that the impedance Z is larger than the threshold value Z1, the control section 102 transmits a signal to the first radio-frequency energy output circuit 104. Further, the output from the first radio-frequency energy output circuit 104 to the first continuous electrode 76 and the second continuous electrode 86 is stopped (STEP 105).

The output from the first radio-frequency energy output circuit 104 to the first continuous electrode 76 and the second continuous electrode 86 is stopped, and the energy is supplied from the second radio-frequency energy output circuit 106 in the energy source 14 to the living tissue (the living tissue in a second region) $L_T$ between the first discrete electrodes 78 and the second discrete electrodes 88 through the cable 28 (STEP 106). Furthermore, the second radio-frequency energy output circuit 106 supplies the set power P2set [W] preset in the display section 108, e.g., a power of approximately 20 [W] to 80 [W] to the living tissue $L_T$ between the first discrete electrodes 78 of the first holding member 62 and the second discrete electrodes 88 of the second holding member 64. It is to be noted that the second radio-frequency energy output circuit 106 is allowed to relatively slowly reach the set power P2set [W] as shown in FIG. 9A in this modification.

Therefore, the second radio-frequency energy output circuit 106 energizes the living tissue $L_T$ as a treatment target between the first discrete electrodes 78 of the first holding member 62 and the second discrete electrodes 88 of the second holding member 64 with a radio-frequency current. That is, the radio-frequency energy is supplied to the living tissue $L_T$ grasped between the electrodes 77 and 78. Therefore, the living tissue $L_T$ is discretely denatured by the first discrete electrodes 78 and the second discrete electrodes 88.

At this time, the impedance Z of the grasped living tissue $L_T$ is measured by the second radio-frequency energy output circuit 106 through the first discrete electrodes 78 and the second discrete electrodes 88. A value of the impedance Z is increased as the radio-frequency current flows through the living tissue $L_T$ and the living tissue $L_T$ is cauterized.

Then, the control section 102 determines whether the impedance Z at the time of output of the radio-frequency energy calculated based on a signal from the second radio-frequency energy output circuit 106 has become equal to or above the threshold value Z2 previously set (STEP 101) in the display section 108 (STEP 107). Moreover, when it is determined that the impedance Z is smaller than the threshold value Z2, the processing returns to STEP 106. That is, the radio-frequency energy for a treatment is kept being supplied to the living tissue $L_T$ grasped between the first discrete electrodes 78 of the first holding member 62 and the second discrete electrodes 88 of the second holding member 64.

When it is determined that the impedance Z is larger than the threshold value Z2, the control section 102 transmits a signal to the second radio-frequency energy output circuit 106. Additionally, the output from the second radio-frequency energy output circuit 106 to the first discrete electrodes 78 and the second discrete electrodes 88 is stopped (STEP 108).

After the output is stopped, the control section 102 generates buzzer sound from the speaker 110 (STEP 109). In this manner, it is possible to readily recognize termination of the treatment for the living tissue $L_T$ given from the first radio-frequency energy output circuit 104 through the first continuous electrode 76 and the second continuous electrode 86 and the treatment for the living tissue $L_T$ given from the second radio-frequency energy output circuit 106 through the first discrete electrodes 78 and the second discrete electrodes 88.

In this modification, although the example where the set power P1set [W] is relatively slowly reached has been explained, the output from the first radio-frequency energy output circuit 104 may rapidly reach the set power P1set [W] as shown in FIG. 9B. Further, the output from the second radio-frequency energy output circuit 106 may have a square waveform.

Besides, as shown in FIG. 9C, it is also preferable to strongly carry out joining/cautery of living tissues by using the first continuous electrode 76 and the second continuous electrode 86 and weakly perform joining/cautery of living tissues by using the first discrete electrodes 78 and the second discrete electrodes 88. In this case, since joining/cautery of the living tissues is weakly performed by the first discrete electrodes 78 and the second discrete electrodes 88, a mutual network of non-denatured living tissues is generated, and a tissue regeneration force of the living tissues can be demonstrated, thereby regenerating tissues around the joined/cauterized tissues on an earlier stage.

[Second Modification of First Embodiment]

A second modification of the first embodiment will now be explained with reference to FIGS. 10A and 10B.

This modification is a modification of the first embodiment, and a description of the same members and members having the same functions as those explained in the first embodiment will be omitted. This can be applied to third and fourth modifications.

As shown in FIG. 10A, the first continuous electrode 76 and the first discrete electrodes 78 are arranged at substantially the same positions as those in the first embodiment depicted in FIG. 3A.

As shown in FIGS. 10A and 10B, a first fluid discharge groove (a continuous electrode fluid discharge groove) 152 is formed as a flow path for a fluid, e.g., steam or a liquid having a high temperature on the outer side of the first continuous electrode 76 in the main body 72 of the first holding member 62. A continuous electrode barrier portion (a dam) 154 is formed on the outer side of the first fluid discharge groove 152 so that the fluid, e.g., steam or a liquid having a high temperature discharged due to a function of the first continuous electrode 76 can enter the first fluid discharge groove 152. As shown in FIG. 10B, the barrier portion 154 protrudes with respect to a plane of the holding surface 72b.

A second fluid discharge groove (a discrete electrode fluid discharge groove) 162 is formed as a flow path for the fluid, e.g., steam or a liquid having a high temperature is formed on an outer periphery of each first discrete electrode 78 in the main body 72. A discrete electrode barrier portion 164 is formed on an outer periphery of the second fluid discharge groove 162 so that the fluid, e.g., steam or a liquid having a high temperature discharged due to a function of each first discrete electrode 78 can enter the second fluid discharge groove 162. As shown in FIG. 10B, the barrier portion 164 protrudes with respect to the plane of the holding surface 72b.

The first fluid discharge groove 152 and the second fluid discharge groove 162 communicate with each other through each communication path 170. Each communication path 170 is formed as a duct. That is, each communication path 170 is formed in the main body 72. Further, each communication path 170 communicates with the cutter guide groove 62a in the base portion 74. That is, the first fluid discharge groove 152 and the second fluid discharge groove 162 communicate with the cutter guide groove 62a in the base portion 74.

It is to be noted that, in the second holding member 64, likewise, a fluid discharge groove (which will be denoted by reference number 172 for the convenience's sake) is formed on the outer side of the second continuous electrode 86 and a barrier portion (which will be designated by reference number 174 for the convenience's sake) is formed on the outer side of the fluid discharge groove 172. Furthermore, a fluid discharge groove (which will be denoted by reference number 182 for the convenience's sake) is formed on an outer periphery of each second discrete electrode 88 of the second holding member 64, and a barrier portion (which will be designated by reference number 184 for the convenience's sake) is formed on an outer periphery of the fluid discharge groove 182. Moreover, the fluid discharge groove 172 on the outer side of the second continuous electrode 86 communicates with the fluid discharge groove 182 on the outer periphery of each second discrete electrode 88 through a communication path (which will be denoted by reference number 190 for the convenience's sake).

A function of the treatment system 10 according to this modification will now be explained.

As explained in the first embodiment, the living tissue $L_T$ as a treatment target is held between the first holding member 62 and the second holding member 64. At this time, the barrier portions 154 and 164 in the main body 72 of the first holding member 62 and the barrier portions 174 and 184 in the main body 82 of the second holding member 64 are pressed against the living tissue $L_T$, and the living tissue $L_T$ comes into contact with the first continuous electrode 76, the second continuous electrode 86, the first discrete electrodes 78, and the second discrete electrodes 88.

In this state, the pedal 16a of the footswitch 16 is operated. The energy is supplied to the first continuous electrode 76, the second continuous electrode 86, the first discrete electrodes 78, and the second discrete electrodes 88 from the energy source 14, respectively. Moreover, the living tissue $L_T$ between the first continuous electrode 76 and the second continuous electrode 86 and between the first discrete electrodes 78 and the second discrete electrodes 88 is heated by the radio-frequency energy. At this time, for example, a fluid, e.g., steam or a liquid is discharged from a heated portion of the living tissue $L_T$.

Here, the first fluid discharge groove 152 in the main body 72 of the first holding member 62 is arranged on the outer side of the first continuous electrode 76, and the second fluid discharge grove 162 is arranged on the outer periphery of each first discrete electrode 78. The first fluid discharge groove 172 in the main body 82 of the second holding member 64 is arranged on the outer side of the second continuous electrode 86, and the second fluid discharge groove 182 is arranged on the outer periphery of each second discrete electrode 88.

Therefore, the fluid discharged due to functions of the first and second continuous electrodes 76 and 86 flows into the cutter guide grooves 62a and 64a and also flows into the first fluid discharge grooves 152 and 172. Additionally, the fluid is prevented from flowing toward the outside by the barrier portions 154 and 174. Therefore, the fluid discharged from the living tissue $L_T$ is confined on the inner sides of the barrier portions 154 and 174, thereby being prevented from flowing toward the outside. That is, each of the barrier portions 154 and 174 plays a role of a dam that prevents the fluid discharged from the living tissue $L_T$ from leaking to the outer sides of the barrier portions 154 and 174.

The fluid discharged due to the functions of the first and second discrete electrodes 78 and 88 flows into the second fluid discharge grooves 162 and 182. Further, the fluid is prevented from flowing to the outside by the barrier portions 164 and 184. Therefore, the fluid discharged from the living tissue $L_T$ is confined on the inner sides of the barrier portions 164 and 184, thereby being prevented from flowing toward the outside. That is, each of the barrier portions 164 and 184 plays a role of a dam that prevents the fluid discharged from the living tissue $L_T$ from leaking toward the outer sides of the barrier portions 164 and 184.

The fluid that has flowed into the second fluid discharge grooves 162 and 182 flows into the first fluid discharge grooves 152 and 172 through the communication paths 170 and 190. Furthermore, this fluid flows toward the base portion 74 of the first holding member 62 and the base portion 84 of the second holding member 64 together with the fluid that has flowed into the first fluid discharge grooves 152 and 172. Moreover, the fluid flows into the cutter guide grooves 62a and 64a communicating with the first fluid discharge grooves 152 and 172 in the base portions 74 and 84. Additionally, although not shown, the first fluid discharge grooves 152 and 172 communicate with each other in the cylindrical body 42 of the shaft 24.

Additionally, the fluid is discharged to the outside of the surgical instrument 12 from the fluid discharge opening 44a of the sheath 44 through the fluid discharge opening 42a of the cylindrical body 42 of the shaft 24.

As explained above, according to this modification, the following effect can be obtained. A description on the same effect as that explained in the first embodiment will be omitted.

When using the surgical instrument 12 to supply the radio-frequency current to the living tissue $L_T$ as the treatment target held in the holding portion 26, even if the fluid discharged from the living tissue $L_T$ as the treatment target flows toward the barrier portions 154 and 164 of the first holding member 62 and the barrier portions 174 and 184 of the second holding member 64 by pressing the barrier portions 154, 164, 174, and 184 against the living tissue $L_T$, the fluid can be led into the first and second fluid discharge grooves 152 and 162 of the first holding member 62, the first and second fluid discharge grooves 172 and 182 of the second holding member 64, and the communication paths 170 and 190.

Therefore, other peripheral tissues can be prevented from being affected by the fluid discharged from a region treated by the radio-frequency energy at the time of giving the living tissue $L_T$ the treatment. That is, a position having an influence when giving the living tissue $L_T$ the treatment can be limited to the living tissue $L_T$ energized with the radio-frequency current between the first continuous electrode 76 and the second continuous electrode 86 and between the first discrete electrodes 78 and the second discrete electrodes 88.

Therefore, according to this modification, discharging the fluid, e.g., steam or a liquid (a biological fluid having a high temperature) generated from the living tissue $L_T$ to the outside of the surgical instrument 12, e.g., the proximal end side of the shaft 24 or the handle 22 side enables suppression of an influence of the fluid, e.g., steam or a liquid (the biological fluid) on living tissues around the living tissue $L_T$ as the treatment target.

In this manner, leading the fluid, e.g., steam or a liquid to a position where it does not come into contact with tissues is important for suppressing a thermal influence on the living tissue $L_T$, and the thermal influence can be prevented from being exercised on the outer side of the holding portion 26 when giving a tissue larger than the holding portion 26 a treatment. That is because, when an open portion (a space) from which a fluid, e.g., steam or a liquid leaks is formed in the holding portion 26 even though the size of the open portion is small, the fluid is discharged from this portion and the living tissue $L_T$ around the holding portion 26 is thermally affected.

Moreover, even if the barrier portions 154, 164, 174, and 184 cover the peripheries of the electrodes (energy discharge sections) 76, 78, 86, and 88 to eliminate such an open portion, the open portion may be formed due to a fluid pressure, e.g., a steam pressure generated from the living tissue $L_T$, and the fluid may be possibly discharged. Therefore, providing the flow paths (the first and second fluid discharge grooves 152, 162, 172, and 182 and the communication paths 170 and 190) that suppress discharge of an unnecessary fluid due to an increase in a fluid pressure and lead the fluid in a predetermined direction to be discharged is useful means.

[Third Modification of First Embodiment]

A third modification of the first embodiment will now be explained with reference to FIG. 10C.

As shown in FIG. 10C, the communication path 170 (which will be referred to as a first communication path hereinafter) is formed as a duct. A duct-like second communication path 170a communicating with the cutter guide groove 62a in the main body 72 is formed in the first communication path 170.

Flowing a fluid generated from the living tissue $L_T$ through the duct-like first and second communication paths 170 and 170a enables preventing, e.g., the fluid possibly having a high temperature from coming into contact with the living tissue $L_T$ as much as possible.

[Fourth Modification of First Embodiment]

A fourth modification of the first embodiment will now be explained with reference to FIGS. 11A to 11D.

As shown in FIGS. 11A to 11C, a side of the main body 72 of the first holding member 62 that is close to the second holding member 64 is flatly formed. A plurality of electrode arrangement portions (concave portions) 72a are discretely formed in the main body 72 of the first holding member 62. Here, the electrode arrangement portions 72a are arranged in four columns in a zigzag pattern in the main body 72.

As shown in FIGS. 11A and 11D, an electrode 202 and a barrier portion 204 are arranged in each electrode arrangement portion 72a. Each electrode 202 is substantially circular, and a through-hole (a steam discharge flow path) 206 is formed at the center of each electrode 202. On the other hand, the barrier portion 204 is arranged on the outer side of each electrode 202.

As shown in FIG. 11D, in each electrode 202, a surface on a side close to the second holding member 64 is placed at a position lower than the barrier portion 204. That is, in the barrier portion 204, a step 204a is formed, and a surface of the electrode 202 is placed at a position lower than a side of the main body 72 of the first holding member 62 close to the second holding member 64.

As shown in FIGS. 11B and 11C, the cutter guide groove (a fluid discharge groove) 62a is formed along the axial direction of the main body 72. A through-hole 206 of each electrode 202 communicates with the cutter guide groove 62a.

As explained above, since the electrode arrangement portions 72a are arranged in the four columns in the zigzag pattern in the main body 72, the electrodes 202 are also arranged in four columns. Here, the electrodes 202 are divided into first electrodes 202a on a side close to the cutter guide groove 62a and second electrodes 202b on a side close to the edge portion of the main body 72. The first electrodes 202a are connected with the first radio-frequency energy output circuit 104 in the energy source 14. The second electrodes 202b are connected with the second radio-frequency energy output circuit 106. It is to be noted that an electrode at the most distal end may belong to either the first electrodes 202a or the second electrodes 202b.

As shown in FIG. 11C, a fluid discharge groove 208 is formed in the main body 72 along the axial direction of the main body 72. The through-hole 206 of each electrode 202 communicates with the fluid discharge groove 208. The fluid discharge groove 208 is formed to be continuous with the cutter guide groove 62a in the base portion 74 of the first holding member 62.

Incidentally, it is preferable for the second holding member 64 to have the same structure as the first holding member 62. In the second holding member 64, reference number 212 (the first electrode 212a, the second electrode 212b) denotes each electrode; reference number 214, the barrier portion; and reference number 216, the through-hole for the convenience's sake.

A function of the treatment system 10 according to this modification will now be explained. Here, a description will be given along the flow depicted in FIG. 8.

As explained in the first embodiment, a living tissue as a treatment target is grasped between the first holding member 62 and the second holding member 64. At this time, the barrier portions 204 and 214 are appressed against the living tissue, and the living tissue is in contact with the first electrodes 202a and 212a and the second electrodes 202b and 212b.

In this state, the pedal 16a of the footswitch 16 is operated. The first radio-frequency energy output circuit 104 in the energy source 14 supplies energy to the first electrodes 202a and 212a. Further, the living tissue $L_T$ between the first electrodes 202a of the first holding member 62 and the first electrodes 212a of the second holding member 64 is heated.

When the living tissue as the treatment target between the first electrodes 202a and 212a is heated in this manner, a fluid, e.g., steam or a liquid is generated from a heated portion of the living tissue.

Here, in a state where the first electrodes 202a of the first holding member 62 are fixed on the inner sides of the barrier portions 204 in the main body 72 of the first holding member 62, surfaces of the first electrodes 202a exposed on the second holding member 64 side are placed at positions slightly lower than the barrier portions 204. Further, the fluid is prevented from leaking to the outside since the barrier portions 204 are appressed against the living tissue. Then, the fluid generated from the living tissue flows into the cutter guide grove 62a through the fluid discharge groove 208 communicating with the through-holes 206 of the first electrodes 202a. Furthermore, this fluid flows toward the base portion 74 of the first holding member 62.

In the second holding member 64, likewise, since the barrier portions 214 are appressed against the living tissue, the fluid generated due to functions of the first electrodes 202a and 212a flows into the cutter guide groove 64a through the fluid discharge groove 218 communicating with the through-holes 216 of the first electrodes 212a.

When the impedance Z measured by the first electrodes 202a and 212a and the first radio-frequency energy output circuit 104 has reached the preset threshold value Z1 at the time of giving a treatment using the first electrodes 202a and 212a in this manner, the output from the first radio-frequency energy output circuit 104 to the first electrodes 202a and 212a is stopped.

Moreover, the second radio-frequency energy output circuit 106 supplies the radio-frequency energy to the living tissue between the second electrodes 202b and 212b through the second electrodes 202b and 212b. When the impedance Z measured by the second electrodes 202b and 212b and the second radio-frequency energy output circuit 106 has reached the preset threshold value Z2, the control section 102 stops the output from the second radio-frequency energy output circuit 106 to the second electrodes 202b and 212b.

After the living tissue is denatured by the first electrodes 202a and 212a in this manner, the living tissue can be denatured by the second electrodes 202b and 212b.

As explained above, according to this modification, the following effect can be obtained.

The electrodes 202 of the first holding member 62 and the second holding member 64 can be divided into the first electrodes 202a and 212a and the second electrodes 202b and 212b to be separately controlled. Therefore, when the treatment for the living tissue using, e.g., the first electrodes 202a in the discretely arranged electrodes 202 is carried out with an increased output and the treatment for the living tissue using the second electrodes 202b in the same is effected with a reduced output, the living tissues can be regenerated by joining the living tissues as the treatment target and pressing the non-denatured living tissues against each other.

When the surgical instrument 12 is used to supply the radio-frequency current to the living tissue as the treatment target grasped by the grasping portion 26, the barrier portions 204 in the first holding member 62 and the barrier portions 214 in the second holding member 64 can be appressed against the living tissue, respectively. Therefore, even if the fluid generated from the living tissue as the treatment target flows toward the barrier portions 204 in the first holding member 62 and the barrier portions 214 in the second holding member 64, the fluid can be led into the cutter guide groove 62a via the through-holes 206 of the first electrodes 202 and the fluid discharge groove 208 and also led into the cutter guide groove 64a via the through-holes 216 of the first electrodes 212 and the fluid discharge groove 218.

Therefore, an influence of the fluid generated from a region energized with the radio frequency at the time of the treatment for the living tissue can be prevented from being exercised on other peripheral tissues. That is, positions at which the influence is exercised at the time of the treatment for the living tissue can be restricted to the living tissue energized with the radio-frequency current between the first electrodes 202a and 212a and the second electrodes 202b and 212b.

Additionally, in the surgical instrument 12 according to this modification, since the plurality of electrodes 202a, 212a, 202b, and 212b are discretely arranged in the first holding member 62 and the second holding member 64, the treatment target can be restricted to a small target. That is, a treatment target range can be limited to falling within each barrier portion 204 or 214, and a living tissue in a part around each barrier portion 204 or 214 can be maintained in a normal state, thereby rapidly curing the treated living tissue.

It is to be noted that the description has been given as to the example where the barrier portions 204 and 214 and the electrodes 202a, 212a, 202b, and 212b are randomly aligned in this modification, but aligning the first electrodes 202a and 212a in particular is also preferable. Further, although the first electrodes 202a are provided on the side close to the cutter guide groove 62a and the second electrodes 202b are provided on the side close to the edge portion of the main body 72 in this modification, various kinds of changes are allowed as long as the electrodes are divided into those connected with the first radio-frequency energy output circuit 104 in the energy source 14 and those connected with the second radio-frequency energy output circuit 106 in the same. For example, the first electrodes may be provided on the distal end side (the side apart from the base portion 74) of the main body 72, and the second electrode may be provided on the side close to the side close to the base portion 74 of the main body 72.

Furthermore, in this modification, although the description has been given as to the example where each of the electrode 202 and the barrier portion 204 is circular, various kinds of changes are allowed. For example, each of the electrode 202 and the barrier portion 204 may be rectangular.

In the first embodiment including these modifications, although the description has been given as to the example of the linear type surgical instrument 12 (see FIG. 1A) that gives a treatment to the living tissue $L_T$ in the abdominal cavity (in the body) through the abdominal wall, an open linear type surgical instrument (treatment instrument) 12a that takes a treatment target tissue to the outside of the body through the abdominal wall to give a treatment may be likewise used as shown in FIG. 12, for example.

The surgical instrument 12a includes a handle 22 and a holding portion 26. That is, as different from the surgical instrument 12 that gives a treatment through the abdominal wall, the shaft 24 (see FIG. 1A) is eliminated. On the other hand, a member having the same function as the shaft 24 is arranged in the handle 22. Therefore, the surgical instrument 12a can be used like the surgical instrument 12 depicted in FIG. 1A.

[Second Embodiment]

A second embodiment will now be explained with reference to FIGS. 13 to 14C. This embodiment is a modification of the first embodiment including various kinds of modifications.

A description will be given as to an example of a circular type bipolar energy instrument (a treatment instrument) 312 that gives a treatment, e.g., through an abdominal wall or outside an abdominal wall.

Figure 13:
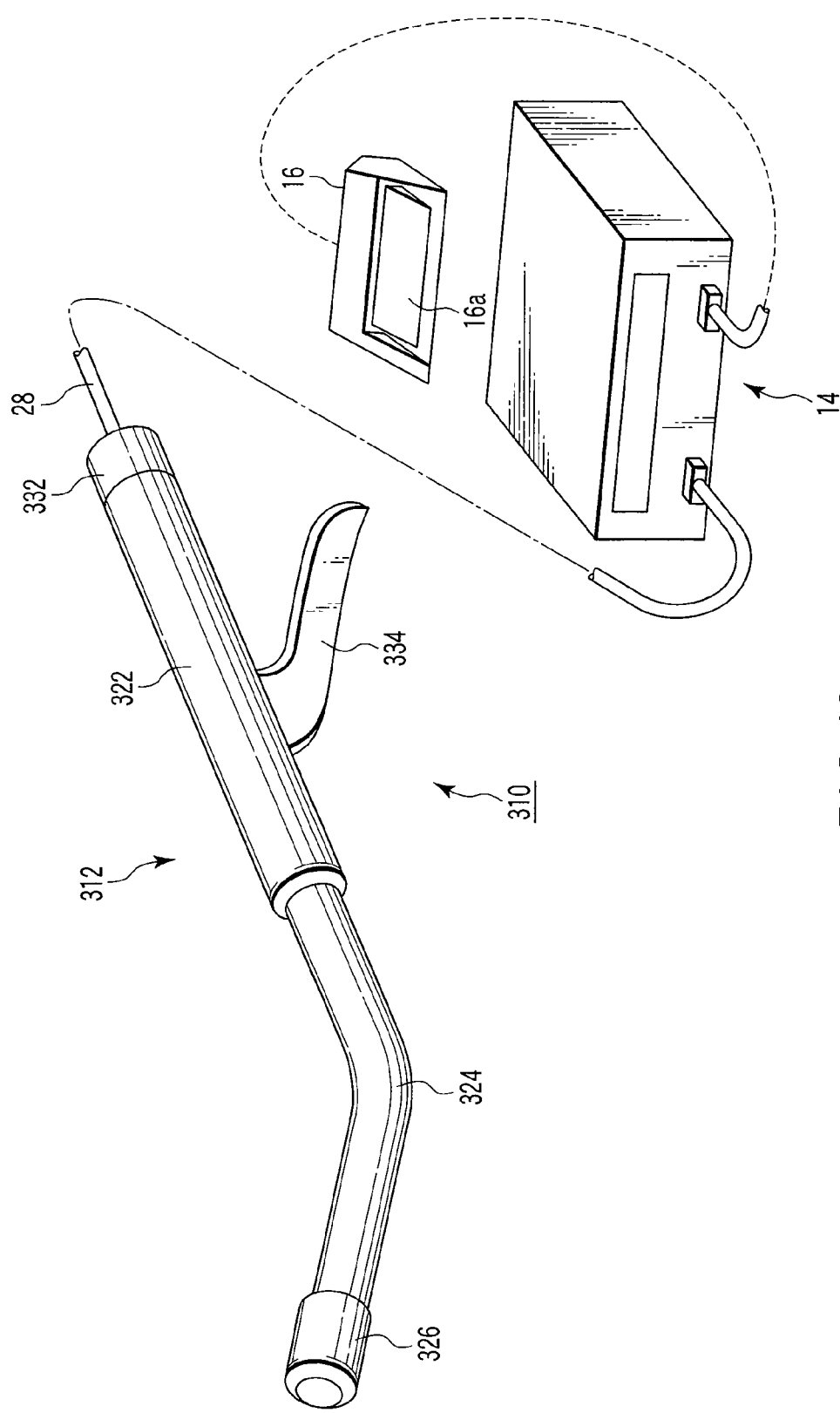
FIG. 13 is a schematic view showing a modification of a treatment system according to a second embodiment.

As shown in FIG. 13, a treatment system 310 includes the energy treatment instrument 312, an energy source 14, and a footswitch 16. The surgical instrument 312 includes a handle 322, a shaft 324, and an openable/closable holding portion 326. The energy source 14 is connected with the handle 322 through a cable 28.

A holding portion opening/closing knob 332 and a cutter driving lever 334 are arranged on the handle 322. The holding portion opening/closing knob 332 is rotatable with respect to the handle 322. When the holding portion opening/closing knob 332 is rotated in, e.g., a clockwise direction with respect to the handle 322, a later-explained detachable side holding portion (a detachable side grasping portion) 344 of the holding portion 326 moves away from a main body side holding portion (a main body side grasping portion) 342. When the same is rotated in a counterclockwise direction, the detachable side holding portion 344 moves close to the main body side holding portion 342.

The shaft 324 is formed into a cylinder. The shaft 324 is appropriately curved while considering insertion properties with respect to a living tissue $L_T$. Of course, forming the shaft 324 straight is also preferable.

Figure 14A:
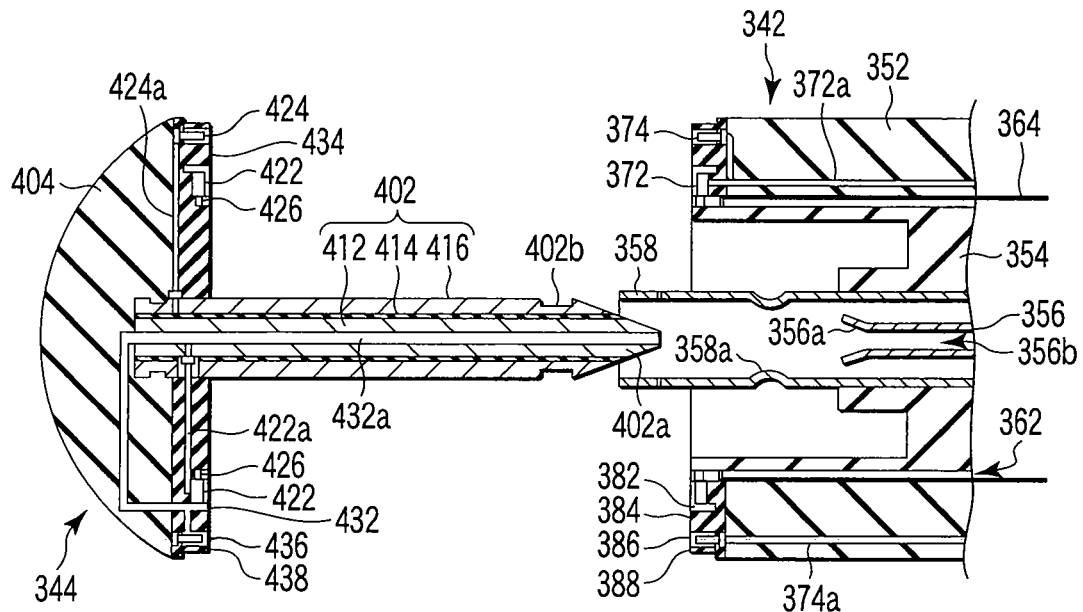
FIG. 14A is a schematic vertical sectional view showing a state in which a main body side holding portion and a detachable side holding portion of the energy treatment instrument according to the second embodiment are separated from each other.
Figure 14B:
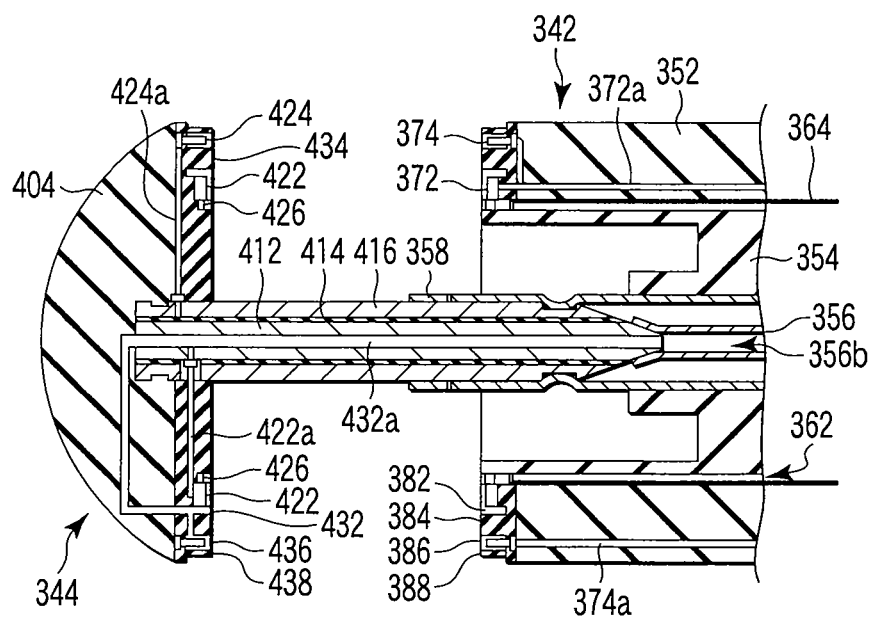
FIG. 14B is a schematic vertical sectional view showing a state where the main body side holding portion and the detachable side holding portion of the energy treatment instrument according to the second embodiment are engaged and the detachable side holding portion is separated from the main body side holding portion.

The holding portion 326 is arranged at a distal end of the shaft 324. As shown in FIGS. 14A and 14B, the holding portion 326 includes the main body side holding portion (a first holding member, a first jaw) 342 formed at the distal end of the shaft 324 and the detachable side holding portion (a second holding member, a second jaw) 344 that is attachable to/detachable from the main body side holding portion 342. In a state where the detachable side holding portion 344 is closed with respect to the main body side holding portion 342, later-explained holding surfaces 384, 388, 434, and 438 of the main body side holding portion 342 and the detachable side holding portion 344 are in contact with each other.

The main body side holding portion 342 includes a cylindrical body 352, a frame 354, a first energization pipe 356, and a second energization pipe 358. The first energization pipe 356 is connected with a first radio-frequency energy output circuit 104 in the energy source 14 through the main body side holding portion 342, the shaft 324, the handle 322, and the cable 28. The second energization pipe 358 is connected with a second radio-frequency energy output circuit 106 in the energy source 14 through the main body side holding portion 342, the shaft 324, the handle 322, and the cable 28 like the first energization pipe 356.

The cylindrical body 352 and the frame 354 have insulating properties. The cylindrical body 352 is coupled with the distal end of the shaft 324. The frame 354 is arranged in a state where it is fixed to the cylindrical body 352.

An opening is formed at a central axis of the frame 354. In the opened central axis of the frame 354, the first energization pipe 356 is arranged to be movable in a predetermined range along the central axis of the frame 354. When the holding portion opening/closing knob 332 is rotated, the first energization pipe 356 can move in the predetermined range due to a function of, e.g., a ball screw (not shown). A diameter expanded portion 356a that is divided into two to expand a diameter as shown in FIGS. 14A to 14C is formed in the first energization pipe 356 to receive a distal end 402a of a later-explained energization shaft 402 in the detachable side holding portion 344. Such a diameter expanded portion 356a enables providing spring properties to a distal end of the first energization pipe 356 and softly holding the distal end 402a of the energization shaft 402.

The second energization pipe 358 is arranged along the central axis of the first energization pipe 356. When the holding portion opening/closing knob 332 is rotated, the second energization pipe 358 can move in a predetermined range together with the first energization pipe 356 due to a function of, e.g., a ball screw (not shown). A protrusion 358a that protrudes toward the inner side in a radial direction is formed on an inner peripheral surface on the distal end side of the second energization pipe 358 so that it can be engaged with/disengaged from a connecting portion 402b of the energization shaft 402.

It is to be noted that the first energization pipe 356 and the second energization pipe 358 are arranged in such a manner that they do not come into contact with each other, but an outer peripheral surface of the first energization pipe 356 is covered with a material having insulating properties. Therefore, even if the first energization pipe 356 and the second energization pipe 358 are prevented from affecting each other even if they come into contact with each other.

As shown in FIGS. 14A and 14B, a cutter guide groove (a first fluid path) 362 is formed between the cylindrical body 352 and the frame 354. A cylindrical cutter 364 is arranged in the cutter guide groove 362. A proximal end portion of the cutter 364 is connected with an outer peripheral surface of a distal end portion of a non-illustrated cutter pusher arranged on a proximal end side of the frame 354. A proximal end portion of the cutter pusher is connected with a cutter driving lever 334 of the handle 322. Therefore, when the cutter driving lever 334 of the handle 322 is operated, the cutter 364 moves through the cutter pusher.

A non-illustrated first fluid ventilation path (a fluid path) communicating with the cutter guide groove 362 is formed between the cutter pusher and the frame 354. Further, a fluid discharge opening (not shown) from which a fluid that has flowed through the first fluid ventilation path is discharged is formed in the shaft 324 or the handle 322.

Figure 14C:
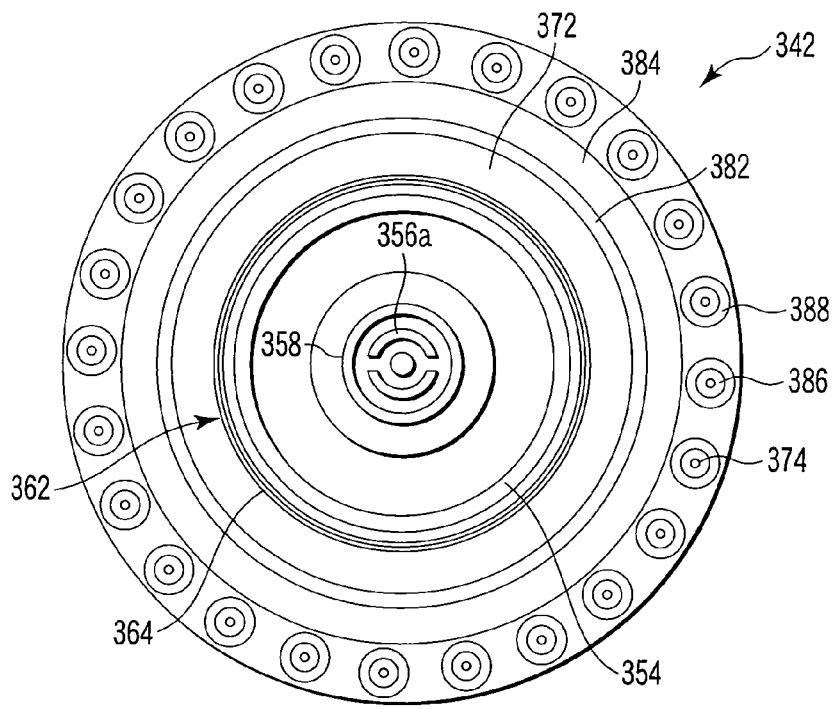
FIG. 14C is a schematic view showing a surface of the main body side holding portion of the energy treatment instrument according to the second embodiment.

As shown in FIGS. 14A to 14C, a first continuous electrode (a sealing member, a first joining member) 372 and a plurality of first discrete electrodes (maintaining members, second joining members) 374 are arranged as output members or energy discharge portions at the distal end of the cylindrical body 232. The first continuous electrode 372 is formed into a seamless continuous annular shape. The first discrete electrodes 374 are discretely arranged on an outer side of the first continuous electrode 372 at predetermined intervals.

A distal end of the first energization line 372a is fixed to the first continuous electrode 372. The first energization line 372a is connected with the cable 28 through the main body side holding portion 342, the shaft 324, and the handle 322. The first discrete electrodes 374 are electrically connected with each other, and a distal end of the second energization line 374a is fixed to one first discrete electrode 374. The second energization line 374a is connected with the cable 28 through the main body side holding portion 342, the shaft 324, and the handle 322.

The first continuous electrode 372 is arranged between an edge portion of the cutter guide groove 246 in which the cutter 242 is arranged and an edge portion of the cylindrical body 232. The first continuous electrode 372 is arranged on a side close to an outer edge portion of the cutter guide groove 246.

The first discrete electrodes 374 having substantially the same shape are arranged along a substantially annular virtual trajectory at substantially equal intervals. Each of the first discrete electrodes 374 is formed into, e.g., a circle. The first discrete electrodes 374 are arranged at substantially predetermined intervals with respect to each other, and each first discrete electrode 374 is arranged at a position apart from the first continuous electrode 372 by an appropriate distance. Each first discrete electrode 374 is placed at a position where a living tissue $L_T$ between the first discrete electrodes 374 adjacent to each other is prevented from being denatured due to heat as much as possible and denaturalization of the living tissue $L_T$ between the first discrete electrodes 374 and the first continuous electrode 372 due to heat is avoided as much as possible.

A steam discharge grove 382 is formed into an annular shape on the outer side of the first continuous electrode 372. That is, the steam discharge groove 382 is formed between the first continuous electrode 372 and the first discrete electrodes 374. The fluid discharge groove 382 communicates with the cutter guide groove 362 in which the cutter 364 is arranged. A holding surface (a tissue contact surface) 384 is formed on an outer side of the fluid discharge groove 382 at a position higher than a surface of the first continuous electrode 372. That is, the holding surface 384 of the main body side holding portion 382 is in close proximity to a later-explained head portion 404 of the detachable side holding portion 344 as compared with the surface of the first continuous electrode 372. Therefore, the holding surface 384 plays a role of a barrier portion (a dam) that prevents a fluid, e.g., steam from flowing to the outer side of the fluid discharge groove 382.

A steam discharge groove 386 is formed into an annular shape on an outer side of each first discrete electrode 374. The fluid discharge groove 386 communicates with the fluid discharge groove 382 arranged on the outer side of the first continuous electrode 372 and the cutter guide groove 362. A holding surface (a tissue contact surface) 388 is formed on an outer side of the fluid discharge groove 386 at a position higher than a surface of each first discrete electrode 374. Therefore, the holding surface 388 plays a role of a barrier portion (a dam) that prevents a fluid, e.g., steam from flowing to the outer side of the fluid discharge groove 386.

On the other hand, the detachable side holding portion 344 includes an energization shaft 402 and the head portion 404 having insulating properties. The energization shaft 402 has a circular cross section, one end formed into a tapered shape, and the other end fixed to the head portion 404. The energization shaft 402 generally has a three-layer structure in which three cylindrical members 412, 414, and 416 are appressed against each other. An inner side (an inner layer) 412 of the energization shaft 402 is a cylindrical member having conducting properties, and an intermediate layer 414 is a cylindrical member having insulating properties, and an outer side (an outer layer) 416 is a cylindrical member having conducting properties.

Furthermore, a distal end (a distal end 402a of the energization shaft 402) of the inner layer 412 is electrically connected with the diameter expanded portion 356a of the first energization pipe 356. A connecting portion (a concave groove portion) 402b that is engaged with the protrusion 358a of the second energization pipe 358 is formed on an outer peripheral surface of the outer layer 416 on a distal end portion side. It is to be noted that covering the part of the outer peripheral surface of the outer layer 416 excluding the connecting portion 402b with a material having insulating properties based on, e.g., coating is preferable.

A second continuous electrode (a sealing member, a first joining member) 422 and second discrete electrodes (maintaining members, second joining members) 424 are arranged in the head portion 404 to face the first continuous electrode 372 and the first discrete electrodes 374 in the main body side holding portion 342. One end of a third energization line 422a is fixed to the second continuous electrode 422. The other end of the third energization line 422a is electrically connected with the inner layer 412 through the outer layer 416 and the intermediate layer 414 of the energization shaft 402. One end of a fourth energization line 424a is fixed to the second discrete electrodes 424. The other end of the fourth energization line 424a is electrically connected with the outer layer 416 of the energization shaft 402.

A cutter receiving portion 426 is formed into an annular shape on the inner side of the second continuous electrode 372 arranged in the head portion 404 to receive a blade of the cutter 364. On the other hand, a fluid discharge groove 432 is formed into an annular shape on an outer side of the second continuous electrode 422. A holding surface (a tissue contact surface) 434 is formed on an outer side of the fluid discharge groove 432 at a position higher than a surface of the second continuous electrode 422. That is, the holding surface 434 of the detachable side holding portion 344 is close to the main body side holding portion 342 as compared with the surface of the second continuous electrode 422. Therefore, the holding surface 434 plays a role of a barrier portion (a dam) that prevents a fluid, e.g., steam from flowing to the outside of the steam discharge groove 432.

A steam discharge groove 436 is formed into an annular shape on an outer side of each second discrete electrode 424. The fluid discharge groove 436 communicates with the fluid discharge groove 432 arranged on the outer side of the second continuous electrode 422. A holding surface (a tissue contact surface) 438 is formed on an outer side of the fluid discharge groove 436 at a position higher than a surface of each second discrete electrode 424. Therefore, the holding surface 438 plays a role of a barrier portion (a dam) that prevents a fluid, e.g., steam from flowing to the outside of the fluid discharge groove 438.

Moreover, the fluid discharge groove 432 communicates with the head portion 404 and a fluid discharge path 432a on an inner side of the inner layer 412 of the energization shaft 402. The fluid discharge path 432a communicates with a fluid ventilation path (a fluid path) 356b in the first energization pipe 356. A fluid discharge opening (not shown) from which a fluid that has flowed through the second fluid ventilation path 356b is discharged to the outside is formed in the shaft 324 or the handle 322.

A function of the treatment system 310 according to this embodiment will now be explained.

An operator previously operates a display section 108 in the energy source 14 shown in FIG. 4 to set output conditions for the treatment system 10 (STEP 1). Specifically, outputs (set powers P1set [W] and P2set [W]) from a first radio-frequency energy output circuit 104 and a second radio-frequency energy output circuit 106, threshold values Z1 and Z2 of an impedance Z of a living tissue $L_T$, and others are set. Here, as shown in FIG. 6A, a description will be given on the assumption that the output (the set power P1set) from the first radio-frequency energy output circuit 104 is set larger than the output (the set power P2set) from the second radio-frequency energy output circuit 106.

In a state where the main body side holding portion 342 is closed with respect to the detachable side holding portion 344, the holding portion 326 and the shaft 324 of the surgical instrument 312 are inserted into, e.g., an abdominal cavity through an abdominal wall. The main body side holding portion 342 and the detachable side holding portion 344 of the surgical instrument 312 are set to face the living tissue $L_T$ as a treatment target.

The grasping portion opening/closing knob 332 of the handle 322 is operated to grasp the living tissue $L_T$ as the treatment target by the main body side holding portion 342 and the detachable side holding portion 344. At this time, the grasping portion opening/closing knob 332 is swiveled in, e.g., a clockwise direction with respect to the handle 322. Then, as shown in FIG. 24A, the energization pipe 356 is moved toward the distal end side with respect to the frame 354 of the shaft 324. Therefore, the living tissue $L_T$ between the main body side holding portion 342 and the detachable side holding portion 344 is increased so that the detachable side holding portion 344 can be detached from the main body side holding portion 342.

Additionally, the living tissue $L_T$ as the treatment target is arranged between the first continuous electrode 372 and the first discrete electrodes 374 of the main body side holding portion 342 and the second continuous electrode 422 and the second discrete electrodes 424 of the detachable side holding portion 344. In this state, the grasping portion opening/closing knob 332 of the handle 332 is swiveled in, e.g., a counterclockwise direction. Therefore, the detachable side holding portion 344 is closed with respect to the main body side holding portion 342. In this manner, the living tissue $L_T$ as the treatment target is held between the main body side holding portion 342 and the detachable side holding portion 344.

In this state, a pedal 16a of the footswitch 16 is operated. A control section 102 in the energy source 14 determines whether the pedal 16a of the switch 16 has been pressed by the operator according to be turned on (STEP 2).

When it is determined that the pedal 16a of the switch 16 has been pressed to be turned on, the first radio-frequency energy output circuit 104 in the energy source 14 supplies the set power P1set preset in the display section 108 to the living tissue (the living tissue in a first region) $L_T$ between the first continuous electrode 372 and the second continuous electrode 422 (STEP 31). At the same time, the second radio-frequency energy output circuit 106 in the energy source 14 supplies radio-frequency energy to the living tissue (the living tissue in a second region) $L_T$ between the first discrete electrodes 374 and the second discrete electrodes 424 (STEP 32).

Therefore, the first radio-frequency energy output circuit 104 energizes the living tissue $L_T$ as the treatment target between the first continuous electrode 372 of the main body side holding portion 342 and the second continuous electrode 422 on the detachable side holding portion 344 with a radio-frequency current. Therefore, Joule heat is generated in the living tissue $L_T$ grasped between the electrodes 372 and 422 so that the living tissue $L_T$ itself is heated. Accordingly, the living tissue $L_T$ is annularly and continuously denatured by the first continuous electrode 372 and the second continuous electrode 422.

At this time, the impedance Z of the grasped living tissue $L_T$ is measured by the first continuous electrode 372, the second continuous electrode 422, and the radio-frequency energy output circuit 104. As shown in FIG. 6B, an impedance Z0 at the start of a treatment is, e.g., approximately 60[Ω]. Further, a value of the impedance Z is increased as the radio-frequency current flows through the living tissue $L_T$ and the living tissue $L_T$ is cauterized.

A fluid (a liquid [blood] and/or a gas [steam]) is discharged from the living tissue $L_T$ as the living tissue $L_T$ is cauterized. At this time, the holding surface 384 of the main body side holding portion 342 and the holding surface 434 of the detachable side holding portion 344 are appressed against the living tissue $L_T$ as compared with the first continuous electrode 372 and the second continuous electrode 422. Therefore, each of the holding surfaces 384 and 434 functions as a barrier portion (a dam) that prevents the fluid from flowing to the outside of the main body side holding portion 342 and the-detachable side holding portion 344.

Accordingly, the fluid discharged from the living tissue $L_T$ is flowed into the cutter guide groove 362 on the inner side of the first continuous electrode 372 from the steam discharge groove 382 on the outer side of the first continuous electrode 372 or directly flowed into the cutter guide groove 362, and flowed through the shaft 324 from the main body side holding portion 342 based on, e.g., suction. The fluid is kept being flowed into the cutter guide groove 362 while the fluid is discharged from the living tissue $L_T$. Therefore, it is possible to avoid the occurrence of thermal spread due to the fluid discharged in a state where a temperature is increased from the living tissue $L_T$, and prevent a portion that is not the treatment target from being affected.

Additionally, the fluid discharged from the living tissue $L_T$ is flowed into the fluid discharge groove 432 on the outer side of the second continuous electrode 422, and further flowed through the shaft 24 from the inside of the first energization pipe 356 via the fluid discharge path 432a formed in the head portion 404 and the energization shaft 402 based on, e.g., suction. The fluid is kept being flowed into the fluid discharge path 432a while the fluid is discharged from the living tissue $L_T$. Therefore, it is possible to avoid the occurrence of thermal spread by the fluid discharged in a state where a temperature is increased from the living tissue $L_T$ and prevent a portion that is not the treatment target from being affected.

Then, the control section 102 determines whether the impedance Z at the time of output of the radio-frequency energy calculated based on a signal from the radio-frequency energy output circuit 104 has become equal to or above the threshold value Z1 (which is approximately 1000[Ω] in this example as shown in FIG. 6B) preset (STEP 1) in the display section 108 (STEP 41). The threshold value Z1 is placed at a position where a previously known increase rate of a value of the impedance Z blunts. Further, when it is determined that the impedance Z is smaller than the threshold value Z1, the processing returns to STEP 31. That is, the radio-frequency energy for the treatment is kept being supplied to the living tissue $L_T$ grasped between the first continuous electrode 372 of the main body side holding portion 342 and the second continuous electrode 422 of the detachable side holding portion 344.

When it is determined that the impedance Z is higher than the threshold value Z1, the control section 102 transmits a signal to the first radio-frequency energy output circuit 104. Furthermore, the output from the first radio-frequency energy output circuit 104 to the first continuous electrode 372 and the second continuous electrode 422 is stopped (STEP 51).

After the output is stopped, the control section 102 generates buzzer sound from a speaker 110 (STEP 61). In this manner, it is possible to easily recognize termination of the treatment with respect to the living tissue $L_T$ given from the first radio-frequency energy output circuit 104 via the first continuous electrode 372 and the second continuous electrode 422.

On the other hand, as explained above, the second radio-frequency energy output circuit 106 in the energy source 14 supplies energy to the living tissue (the living tissue in the second region) $L_T$ between the first discrete electrodes 78 and the second discrete electrodes 88 (STEP 32).

Moreover, the second radio-frequency energy output circuit 106 supplies the set power P2set [W] preset in the display section 108 to the living tissue $L_T$ between the first discrete electrodes 374 of the main body side holding portion 342 and the second discrete electrodes 424 of the detachable side holding portion 344. It is to be noted that the output from the second radio-frequency energy output circuit 106 to the first discrete electrodes 374 and the second discrete electrodes 424 may be larger than or smaller than the output from the first radio-frequency energy output circuit 104 to the first continuous electrode 372 and the second continuous electrode 422. Such magnitudes of the outputs are appropriately set before the treatment in accordance with a treatment target, an object, and others (STEP 1).

Therefore, the radio-frequency current flows through the living tissue $L_T$ grasped between the main body side holding portion 342 and the detachable side holding portion 344, and heat is generated in the living tissue $L_T$ by a function of Joule heat to start cauterization (denaturalization of the tissue) of the tissue. Then, the first discrete electrodes 374 and the second discrete electrodes 424 discretely denature the living tissue $L_T$ between these discrete electrodes 374 and 424. At this time, the impedance Z of the grasped living tissue $L_T$ is measured by the second radio-frequency energy output circuit 106 through the first discrete electrodes 374 and the second discrete electrodes 424. As shown in FIG. 6B, an impedance Z0 at the start of the treatment is, e.g., approximately 60[Ω]. Additionally, a value of the impedance Z is increased as the radio-frequency current flows through the living tissue $L_T$ and the living tissue $L_T$ is cauterized.

A fluid (e.g., a liquid [blood] and/or a gas [steam]) is discharged from the living tissue $L_T$ as the living tissue $L_T$ is cauterized in this manner. At this time, the holding surface 388 of the main body side holding portion 342 and the holding surface 438 of the detachable side holding portion 344 have high adhesion degrees with respect to the living tissue $L_T$ as compared with the first discrete electrodes 374 and the second discrete electrodes 424. Therefore, each of the holding surfaces 388 and 438 functions as a barrier portion (a dam) that suppresses the fluid from flowing toward the outside of the main body side holding portion 342 and the detachable side holding portion 344.

Therefore, the fluid discharged from the living tissue $L_T$ is flowed into the cutter guide groove 362 on the inner side of the first continuous electrode 372 from the steam discharge groove 386 on the outer periphery of each first discrete electrode 374 and further flowed through the shaft 24 from the main body side holding portion 342 based on, e.g., suction. The fluid is kept flowing into the cutter guide groove 62a while the fluid is discharged from the living tissue $L_T$. Therefore, it is possible to avoid the occurrence of thermal spread due to the fluid discharged in a state where a temperature is increased from the living tissue $L_T$ and prevent portions which are not the treatment target from being affected.

Further, the fluid discharged from the living tissue $L_T$ is flowed into the steam discharge groove 432 communicating with the steam discharge groove 436 on the outer periphery of each second discrete electrode 424 and further flowed through the shaft 24 from the inside of the first energization pipe 356 through the fluid discharge path 432a formed in the head portion 404 and the energization shaft 402 based on, e.g., suction. The fluid is kept flowing into the fluid discharge path 432a while the fluid is discharged from the living tissue $L_T$. Therefore, it is possible to avoid the occurrence of thermal spread due to the fluid discharged in a state where a temperature is increased from the living tissue $L_T$ and prevent portions which are not the treatment target from being affected.

Then the control section 102 determines whether the impedance Z at the time of output of the radio-frequency energy calculated based on a signal from the second radio-frequency energy output circuit 106 has become equal to or above the present threshold value Z2 (which is approximately 1000[Ω] as shown in FIG. 6B) (STEP 42). It is preferable for the threshold value Z2 to be set at a position where a previously known increase rate of a value of the impedance Z blunts. Furthermore, when it is determined that the impedance Z is smaller than the threshold value Z2, the processing returns to STEP 32. That is, the radio-frequency energy for the treatment is kept being supplied to the living tissue $L_T$ grasped between the first discrete electrodes 374 of the main body side holding portion 342 and the second discrete electrodes 424 of the detachable side holding portion 344.

When it is determined that the impedance Z is higher than the threshold value Z2, the control section 102 transmits a signal to the second radio-frequency energy output circuit 106. Moreover, the output from the second radio-frequency energy output circuit 106 to the first discrete electrodes 374 and the second discrete electrodes 424 is stopped (STEP 52).

Additionally, after the output is stopped, the control section 102 generates buzzer sound from the speaker 110 (STEP 62). It is possible to easily recognize termination of the treatment for the living tissue $L_T$ given from the second radio-frequency energy output circuit 106 through the first discrete electrodes 374 and the second discrete electrodes 424.

Figures 15A, 15B:
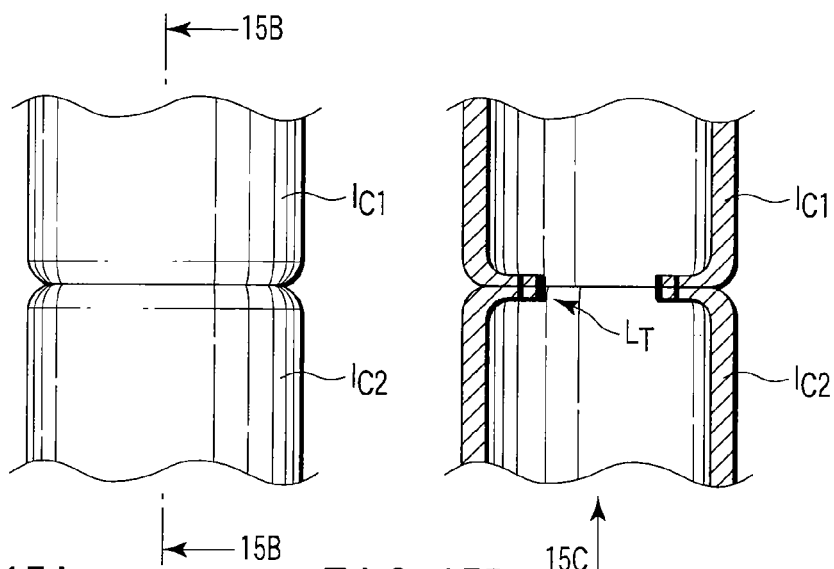
FIG. 15A is a schematic view showing a state where intestinal canals are joined by using the energy treatment instrument according to the second embodiment.
FIG. 15B is a schematic vertical sectional view showing a state where the intestinal canals are joined by using the energy treatment instrument according to the second embodiment taken along a line 15B-15B in FIG. 15A.
Figure 15C:
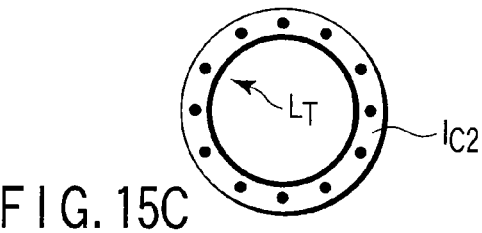
FIG. 15C is a schematic view showing that a state where the intestinal canals are joined by using the energy treatment instrument according to the second embodiment is observed from a direction of an arrow 15C in FIG. 15B.

A description will now be given as to an example where the treatment system 310 having such a function is used to join intestinal canals $I_{C1}$ and $I_{C2}$ of a small intestine which are aligned in, e.g., an axial direction so that they are sealed as shown in FIGS. 15A to 15C.

The display section 108 in the energy source 14 is operated to set the outputs (P1set and P2set) from the first radio-frequency energy output circuit 104 and the second radio-frequency energy output circuit 106 in advance.

The pair of intestinal canals $I_{C1}$ and $I_{C2}$ facing each other in the axial direction are held by the holding surfaces 384 and 388 of the main body side holding portion 342 and the holding surfaces 434 and 438 of the detachable side holding portion 344 to sandwich wall surfaces of both the intestinal canals $I_{C1}$ and $I_{C2}$ at end portions thereof.

In this state, when the pedal 16a of the footswitch 16 is pressed, the energy is supplied to living tissues $L_T$ between the first continuous electrode 372 and the second continuous electrode 422 and between the first discrete electrodes 374 and the second discrete electrodes 424. Therefore, the first continuous electrode 372, the second continuous electrode 422, the first discrete electrodes 374 and the second discrete electrodes 424 heat the intestinal canals $I_{C1}$ and $I_{C2}$ to be denatured.

Moreover, when the living tissues $L_T$ between the first continuous electrode 372 and the second continuous electrode 422 have reached the predetermined threshold value Z1, the output from the first radio-frequency energy output circuit 104 is stopped. When the living tissues $L_T$ between the first discrete electrodes 374 and the second discrete electrodes 424 have reached the predetermined threshold value Z2, the output from the second radio-frequency energy output circuit 106 is stopped.

When the impedance Z of the living tissues $L_T$ between the first continuous electrode 372 and the second continuous electrode 422 has reached the predetermined threshold value Z1, the first continuous electrode 372 and the second continuous electrode 422 heat and denature the intestinal canals $I_{C1}$ and $I_{C2}$ to be joined. That is, the first continuous electrode 372 and the second continuous electrode 422 annularly seal the end portions of the intestinal canals $I_{C1}$ and $I_{C2}$. When the impedance Z of the living tissues $L_T$ between the first discrete electrodes 374 and the second discrete electrodes 424 has reached the predetermined threshold value Z2, the first discrete electrodes 374 and the second discrete electrodes 424 heat and denature the intestinal canals $I_{C1}$ and $I_{C2}$ to be joined. That is, the first discrete electrodes 374 and the second discrete electrodes 424 discretely join the living tissues on the outer side of the annularly sealed portions at the end portions of the intestinal canals $I_{C1}$ and $I_{C2}$ in such a manner that the living tissues are appressed against each other. In this manner, the intestinal canals $I_{C1}$ and $I_{C2}$ are continuously and discretely denatured and joined (anastomosed).

Additionally, the cutter driving knob 334 shown in FIG. 13 is operated to move forward the cutter 364 along the cutter guide groove 362 from the state depicted in FIG. 14B while grasping the intestinal canals $I_{C1}$ and $I_{C2}$ between the main body side holding portion 342 and the detachable side holding portion 344. As the cutter 364 moves forward, the blade at the distal end of the cutter 364 circularly cuts the inside of the regions denatured and joined by the first continuous electrode 372 and the second continuous electrode 422. Therefore, as shown in FIG. 15C, the substantially circularly sealed portions of the wall surfaces of the intestinal canals $I_{C1}$ and $I_{C2}$ are cut, thereby maintaining a circular communicating state of the intestinal canals $I_{C1}$ and $I_{C2}$.

In this state, the cutter driving knob 334 is operated to move backward the cutter 364. Then, the holding portion opening/closing knob 332 of the handle 322 is operated to open the main body side holding portion 342 and the detachable side holding portion 344. At this time, for example, as shown in FIG. 15C, the outer side of the portions continuously joined by the first continuous electrode 372 and the second continuous electrode 422 is discretely denatured. At this time, as explained above, since the output supplied from the second radio-frequency energy output circuit 106 to the first discrete electrodes 374 and the second discrete electrodes 424 has been set high, the discretely denatured and joined portions are firmly coated and thereby have pealing resistance.

Therefore, a region where the living tissues are denatured by the first discrete electrodes 374 and the second discrete electrodes 424 makes a significant contribution to more assuredly press the living tissues against each other. Although a force may act in a direction along which joining of the intestinal canals $I_{C1}$ and $I_{C2}$ is released, the region where the living tissues are denatured by the first discrete electrodes 374 and the second discrete electrodes 424 makes the significant contribution to press the living tissues against each other. Therefore, a mutual network of non-denatured living tissues of the intestinal canals $I_{C1}$ and $I_{C2}$ is generated, and a tissue regeneration force for the living tissues is demonstrated, thereby regenerating the living tissues of the intestinal canals $I_{C1}$ and $I_{C2}$ on an earlier stage.

As explained above, according to this embodiment, the following effect can be obtained.

The continuous electrodes 372 and 422 and the discrete electrodes 374 and 424 are arranged in the main body side holding portion 342 and the detachable side holding portion 344, and output amounts, output timings, and others of the energy input to the continuous electrodes 372 and 422 and the energy input to the discrete electrodes 374 and 424 are separately set. Additionally, appropriately setting the output amounts, the output timings, and others in accordance with a treatment target enables setting and effecting an optimum treatment with respect to the treatment target.

Further, in this embodiment, the description has been given as to the example using the bipolar type surgical instrument 312, but giving a monopolar type radio-frequency treatment as shown in FIG. 3E explained in the first embodiment is also preferable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system which is configured to apply energy to a living tissue to treat the living tissue, comprising:
   a pair of holding members, each having a holding surface configured to hold at least two living tissues;
   a cutter guide groove configured to guide and take a cutter to cut the living tissues inside and outside with respect to the holding face;
   a sealing member provided without discontinuity on the holding surface surrounding the cutter guide groove and configured to join desired regions of the at least two living tissues when one of a high frequency energy or thermal energy is applied;

a maintaining member provided on the holding surface at a side opposite of the cutter guide groove with respect to the sealing member and which the maintaining member maintains joining by discontinuous joining the living tissues when one of the high frequency energy or thermal energy is applied to the living tissues near the region sealed by the sealing member when it is in a state of contact;

a first output circuit which is configured to switch supplying or non-supplying of one of the high frequency energy or the thermal energy to the sealing member, depending on a first impedance of the living tissues, obtained with supplying one of the high frequency energy or the thermal energy to the sealing member;

a second output circuit which is configured to switch supplying or non-supplying of one of the high frequency energy or the thermal energy to the maintaining member, depending on the second impedance of the living tissues, obtained with supplying the high frequency energy or the thermal energy to the maintaining member;

a control section which is configured to control the first output circuit and the second output circuit, the control section comparatively determining the first impedance or the second impedance with a predetermined impedance and controlling the supply of one of the high frequency energy or the thermal energy from the first circuit or the second circuit output.

2. The treatment system according to claim 1, wherein the sealing member and/or the maintaining member are away from each other to provide a physical function to the at least two living tissues.

3. The treatment system according to claim 1, wherein
the sealing member has a continuous member and provides a mechanical/physical function to the at least two living tissues, and
the maintaining member has a plurality of discontinuous members to maintain a state where the at least two living tissues are in contact with each other by providing the physical function to the living tissues.

4. The treatment system according to claim 1, wherein each of the sealing member and the maintaining member includes at least one of a radio-frequency electrode and a heater.

5. The treatment system according to claim 1, wherein at least one of the sealing member and the maintaining member is provided on the pair of holding members.

6. The treatment system according to claim 1, wherein the control section determines an output amount of an energy output from the sealing member by the first control section is different from an output amount of an energy output from the maintaining member by the second control section.

7. A treatment system which is configured to apply energy to a living tissue to treat the living tissue, comprising:
a pair of holding members each having a holding surface configured to hold at least two living tissues;
a cutter guide groove configured to guide and take a cutter to cut the living tissues inside and outside with respect to the holding face;
a handle which is operated to relatively move at least one of the holding surfaces with respect to the other;
a first joining member provided without discontinuity on the holding surface surrounding the cutter guide groove and the joining member is configured to join a predetermined region of the at least two living tissues when one of a high frequency energy or thermal energy is applied to the desired sealed regions of the at least two living tissues;
a second joining member which is provided opposite to the cutter guide groove with respect to the first joining member on the holding surface and which second joining member is configured to discontinuously join the living tissues when one of the high frequency energy or the thermal energy is applied to the living tissues near the region joining by the first joining member when it is in a state of contact;
a first output circuit configured to switch supplying or non-supplying of one of the high frequency energy or the thermal energy to the first joining member depending on a first impedance of the living tissues obtained by supplying the high frequency energy or the thermal energy to the first joining member;
a second output circuit configured to switch supplying or non-supplying of one of the high frequency energy of the thermal energy to the second joining member depending on the second impedance of the living tissues obtained by supplying the high frequency energy or the thermal energy to the second joining member;
a control section which controls the first output circuit and the second output circuit, the control section comparatively determining the first impedance or the second impedance with a predetermined impedance and controlling the supply of the high frequency energy or the thermal energy from the first output circuit or the second output circuit;
at least one first control section which controls an output of energy that is applied to the first joining member; and
at least one second control section which controls an output of energy that is applied to the second joining member.

8. The treatment system according to claim 7, wherein the first joining member includes at least one electrode arranged on at least one of the holding surfaces, and
the second joining member includes a plurality of electrodes arranged near the first joining member.

9. The treatment system according to claim 7, further comprising:
at least one barrier portion provided to be adjacent to at least one of the first joining member and the second joining member, the barrier portion being placed at a position equal to or higher than the first joining member and the second joining member.

10. The treatment system according to claim 7, wherein the holding member has a flow path, i.e., a groove or a duct which is provided near at least one of the first joining member and the second joining member and allows a fluid generated from the living tissues held by the pair of holding members to flow therethrough.

11. The treatment system according to claim 7, wherein
the first joining member includes at least one of a radio-frequency electrode and a heater to seal the living tissues, and
the second joining member includes at least one of a radio-frequency electrode and a heater to maintain and join vicinities of the living tissues sealed by the first joining member.

* * * * *